United States Patent [19]
Szostak et al.

[11] Patent Number: 5,631,146
[45] Date of Patent: May 20, 1997

[54] DNA APTAMERS AND CATALYSTS THAT BIND ADENOSINE OR ADENOSINE-5'-PHOSPHATES AND METHODS FOR ISOLATION THEREOF

[75] Inventors: Jack W. Szostak, Boston; David E. Huizenga, Winthrop, both of Mass.

[73] Assignee: The General Hospital Corporation, Boston, Mass.

[21] Appl. No.: 375,116

[22] Filed: Jan. 19, 1995

[51] Int. Cl.$^6$ .............................. C12P 19/34; C12Q 1/68; C07H 21/04; A61K 48/00
[52] U.S. Cl. ............................... 435/91.1; 435/6; 435/5; 536/24.3; 536/24.5; 514/44
[58] Field of Search ................... 435/91.1, 6, 5; 536/24.3, 24.5; 514/44

[56] References Cited

U.S. PATENT DOCUMENTS

| | | | |
|---|---|---|---|
| 5,037,746 | 8/1991 | Cech et al. | 435/91 |
| 5,116,742 | 5/1992 | Cech et al. | 435/91 |
| 5,180,818 | 1/1993 | Cech et al. | 536/23.1 |
| 5,270,163 | 12/1993 | Gold et al. | 435/6 |

FOREIGN PATENT DOCUMENTS

| | | |
|---|---|---|
| WO96/06944 | 3/1996 | WIPO. |
| WO96/06950 | 3/1996 | WIPO. |

OTHER PUBLICATIONS

Bartel et al., "HIV-1 Rev Regulation Involves Recognition of Non-Watson-Crick Base Pairs in Viral RNA," Cell 67:529-536,1991.
Bartel et al., "Isolation of New Ribozymes From a Large Pool of Random Sequences," Science 261, 1411-1418, 1993.
Beaudry et al., "Directed Evolution of an RNA Enzyme," Science 257, 635-641, 1992.
Been et al., "Group I Intron Self-Splicing With Adenosine: Evidence for a Single Nucleoside-Binding Site," 252, Science 434-437, 1990.

Benner et al., "Modern Metabolism as a Palimpsest of the RNA World," Proc. Natl. Acad. Sci. USA 86, 7054-7058, 1989.
Bock et al., "Selection of Single-Stranded DNA Molecules That Bind and Inhibit Human Thrombin, " Nature 355, 564-566, 1992.
Breaker et al., "A DNA Enzyme That Cleaves RNA," Chemistry & Biology 1, 223-229, 1994.
Connell et al., "Three Small Ribooligonucleotides With Specific Arginine Sites," Biochemistry 32, 5497-5502, 1993.
Ellington et al., "In Vitro Selection of RNA Molecules That Bind Specific Ligands," Nature 346, 818-822 1990.
Ellington et al., "Selection In Vitro of Single-Stranded DNA Molecules That Fold Into Specific Ligand-Binding Structures," Nature 355, 850-852, 1992.
Famulok et al., "Stereospecific Recognition of Tryptophan Agarose by In Vitro Selected RNA," J. Am. Chem. Soc. 114, 3990-3991, 1992.
Famulok, "Molecular Recognition of Amino Acids by RNA-Aptamers: An L-Citrulline Binding RNA Motif and Its Evolution Into an L-Arginine Binder," J. Am. Chem. Soc. 116, 1698-1706, 1994.
Gibbons, "Molecular Scissors: RNA Enzymes Go Commercial," Research News, 521, 1991.
Green et al., "Selection of a Ribozyme That Functions as a Superior Template in a Self-Copying Reaction," Science 258, 1910-1915, 1992.

(List continued on next page.)

Primary Examiner—W. Gary Jones
Assistant Examiner—Dianne Rees
Attorney, Agent, or Firm—Karen Lech Elbing

[57] ABSTRACT

Disclosed are single-stranded DNA molecules which bind adenosine or an adenosine-5'-phosphate and methods for their production and isolation. Also disclosed are methods for producing and isolating related catalytic DNA molecules.

12 Claims, 17 Drawing Sheets

OTHER PUBLICATIONS

Jenison et al., "High-Resolution Molecular Discrimination by RNA," Science 263, 1425–1429, 1994.

Joyce, G., "RNA Evolution and the Origins of Life," Nature 338, 217–224, 1989.

Lehman et al., "Evolution In Vitro of an RNA Enzyme With Altered Metal Dependence," Nature 361, 182–185, 1993.

Lorsch et al., "In Vitro Selection of RNA Aptamers Specific for Cyanocobalamin," Biochemistry 33, 973–982, 1994.

Pan et al., "In Vitro Selection of RNAs That Undergo Autolytic Cleavage with $Pb^{2+}$," Biochemistry 31, 3887–3895, 1992.

Sassanfar et al., "An RNA Motif That Binds ATP," Nature 364, 550–553, 1993.

Sen et al., "Guanine Quartet Structures," Methods in Enzymology 211, 191–199, 1992.

Tsai et al., "In Vitro Selection of an RNA Epitope Immunologically Cross-Reactive With a Peptide," Proc. Natl. Acad. Sci. USA 89, 8864–8868, 1992.

Tuerk et al., "Systematic Evolution of Ligands by Exponential Enrichment: RNA Ligands to Bacteriophage T4 DNA Polymerase," Science 249, 505–510, 1990.

Wilson et al., "Ribozyme Catalysis," Current Opinion in Structural Biology 2, 749–756, 1992.

Lauhon et al. J. of American Chemical Soc. 117: 1246–1257 1995.

Huizenga et al. Biochemistry 34: 656–665 1995.

```
              CONSERVED              CONSERVED
              REGION 1               REGION 2
         P1  ╭─────╮  P2        P2' ╭─────╮  P1'
WT     GTGCTTGGGCGAGTATT---GCGGACGAAAGCGGCCCTGCTGAAG
 1     GTGCTTGGGCGAATATT---GTGGACGAAAGCGGCCTGCCACCAG
 5     ATGCTTGGGGGAGGAAT---GCGGAGGAAATTAGTCTGGTGCGG
 6     TCGATTGGGCGAGTATT---GCGGTGGAAATCGAGGTTGATTAAT
 8     ATGCTTGGGCGAGGCTT---TCGGACGAAAGCGTCGGTCGTGTCG
10     TTGCTTGGGCGAGTATT---TCGGACGAAAGCAGTGCTGCTAAAG
37     TTGCTTGGGCGAG-CGT---ACGAGGAAAGCCTCCCTGTCTGACTG
38     GTGCTTGGCCGAGTAGA---ATGCACGAAAGCGCGATTGTTGCAA
44     GCGTTTGGCGCAGGAGA---ACGGAGGAAAACGGCCGCCCTGAGT
46     GTGCTTGGGGGAGTACT---GCGGGGGAGAGCGACCGTGCTGGTC
45     TTGCCTGGGGCAACATT---GTGCACGAAGCAGGGTGTAGTGGGC
42     AAGCATGGGCGAGTCTT---GCGCAGGAATGCGCACCACGTGTCG
11  TGGTTTTCGGGCGAGTCTG---A-GCACGAAAACGCCACGGCTAACG
41     CTGATTGGAGGAGTATT---GCGGGGGAAATCGGGCTGCTAAAG
43     ATGATTGGAGCAGCATC---GCGGGGAAGGGGCTCTGCTAAAG
14     GTGATTGGCCGAGCATT---GCGAGGAAAAATGCGCGTGTGATG
16     CTACCTGGGCGAGCATT---GGGCACGAAGGTAGCCGTGCGAAAA  2
17      AAGTTGGCCGAGTATT---GCGAGGAAAAGCTGCACTACAGGTG
20     AAGCTCGGCGGAGTATC---GCGGAGGAGAGCGGCTAAGATTATG
22     CTGCTTGGACGAGAATC---GCGGGGGAAAGAGGATGTGCTCAAA
23      GACTTGGGCGAGCATT---GCGAGCAAAACGGCGCAGAACAAC
21     CTACCTGGGGGAGCATT---GGGGACGAAGGTAGCCGTGCGAAAA
47     GTGCGTGGGCGAAAATT---TTGGAGGAATGCGACGCTGCTGAA
52     GTGATTGGCGGAGCATA---GCGGAGGAAATCAACCCTACTGAAC
54     GTCCTTGGCGCAGCGTA---CAGGGAAAACGCGGTAATCATGATG
55     GTTCTTGGCGCAGTAGT---ACGGAGGAAAGCAGTCGTGATATGG
58     GTGATTGGGCGAATATT---GTGGAGGAAAGAAGCCGTGCCGACC
59     TATCTTGGGCGAACATG---CTGGCGGAAAGCTAGAGTGCTCAAA
60     ATGCGTGGGGGAGCATT---ACGCAGGAACGCTTGCTTGCTGAAC
66     GAGCTCGGGCGAGTATT---ATGCACGAGAGCGACCTTGCTGACG
68     ACACTTGGAGGAGTATG---GCGGGGGAGAGTAGCAGTTCCGAAT
69     TCGATTGGGCGAATAAC---GTGGAGGAAATCGCCTATTCTGAAG
70     CACTTTGGCGGAGTCTT---GCGGAGGAGAACGTGCGTGCAGACC
72     TTGCGTGGGGGAACATT---GTGGAGGAACGCGGCCGTACAGATG
73      GTTTTGGGCGAGAATT---TCGGAGGAAAGCAAGGTCGTGCTTAG
74     GCGCTTGGGCGAAAATT---GTGGAGGAAAGCACCCCAGTTGTTA
77     GAGCTTGGGCGAGCATT---GCGAGGGAAGCTGGGGTGTTTATG
78     GGCAGTGGGGGAGGAAT---GCGGAGGAATGTAGCCCGGTGGAAG
79     GTGCTTGGGCGAGTATT---GTGGAGGAAAGCACACCTGTTCACG
80     GTGGTTGGGCGAGCAAT---GCGAGGAAATCCGGTGCGCTGAATC
39       GATCGGGCGAGAGAATA-GCGGACGAGATCGTCCCTGCTGAGG
28     GTGCTCGGGCGAACCTTGTGGAGGAAGCGCATTACGGTGTTT
31     GTGCATGGCCGAGTATG--ACGGGCGAATGCAGCCCGGATGAAG
56     CTTTTTGGGCGAGTATTT--ACGGACGAAAATTGCAGTGACTGAAC
67     CTTGTTGGGCGAGTACTA---CGGGAGGAAACAGGGTTCCTGAAG
```

Fig. 4A

DH25.42      C*CTGGGGGA*GT---ATT*GC*GGAGGA*AGG*      ++

Fig. 5A

DH21.90       *TGGGGGA*GT---ATT*GC*GGAGGA*A*         +
DH23.60      *CTGGGGGA*GT---ATT*GC*GGAGGA*AG*        +
DH25.42      *CCTGGGGGA*GT---ATT*GC*GGAGGA*AGG*      ++
DH27.54      *TCCTGGGGGA*GT---ATT*GC*GGAGGA*AGGA*    ++

DH23.45      *CCTGGGGGAC*-----ATT*G*GGAGGAAGG        +
DH23.59      *CCTGGGGGAG*-----ATT*C*GGAGGAAGG        +
DH24.89      *CCTGGGGGAC*----ATT*GG*GAGGAAGG         +
DH25.40      *CCTGGGGGAGC*---ATT*GG*GAGGAAGG         ++
DH25.41      *CCTGGGGGAGC*---ATT*GC*GGAGGAAGG        ++
DH25.42      *CCTGGGGGAGT*---ATT*GC*GGAGGAAGG        ++
DH27.53      *CCTGGGGGAGCT*-ATT*AGC*GGAGGAAGG        +
DH26.39      *CCTGGGGGAGAG*--ATT*CT*GGAGGAAGG        +
DH27.47      *CCTGGGGGAGAG*-ATTA*CT*GGAGGAAGG        ++
DH28.35      *CCTGGGGGAGTAG*ATTC*T*AGGAGGAAGG        +/-

Fig. 5B

```
DH25.95       CCTAGGGGAGT---ATTGCGGAGGAAGG   ++
DH25.67    deaCCTGGGGGAGT---ATTGCGGAGGAAGG   +
DH25.7606meCCTGGGGGAGT---ATTGCGGAGGAAGG     +
DH25.103      CCTIGGGGAGT---ATTGCGGAGGAAGG   -

DH25.96       CCTGAGGGAGT---ATTGCGGAGGAAGG   +
DH25.68    deaCCTGGGGGAGT---ATTGCGGAGGAAGG   -
DH25.7706meCCTGGGGGAGT---ATTGCGGAGGAAGG     +
DH25.107      CCTGIGGGAGT---ATTGCGGAGGAAGG   +

DH25.97       CCTGGGAGAGT---ATTGCGGAGGAAGG   -
DH25.70    deaCCTGGGGGAGT---ATTGCGGAGGAAGG   +
DH25.7906meCCTGGGGGAGT---ATTGCGGAGGAAGG     -
DH25.121      CCTGGGIGAGT---ATTGCGGAGGAAGG   +

DH25.113      CCTGGGGAAGT---ATTGCGGAGGAAGG   -
DH25.71    deaCCTGGGGGAGT---ATTGCGGAGGAAGG   +
DH25.8006meCCTGGGGGAGT---ATTGCGGAGGAAGG     +/-
DH25.122      CCTGGGGIAGT---ATTGCGGAGGAAGG   -

DH25.98       CCTGGGGGAGT---ATTGCAGAGGAAGG   -
DH25.72    deaCCTGGGGGAGT---ATTGCGGAGGAAGG   +
DH25.8106meCCTGGGGGAGT---ATTGCGGAGGAAGG     +
DH25.123      CCTGGGGGAGT---ATTGCIGAGGAAGG   +

DH25.43       CCTGGGGGAGT---ATTGCGAAGGAAGG   -
DH25.73    deaCCTGGGGGAGT---ATTGCGGAGGAAGG   -
DH25.8206meCCTGGGGGAGT---ATTGCGGAGGAAGG     +
DH25.124      CCTGGGGGAGT---ATTGCGIAGGAAGG   +

DH25.99       CCTGGGGGAGT---ATTGCGGAAGAAGG   -
DH25.74    deaCCTGGGGGAGT---ATTGCGGAGGAAGG   +
DH25.8306meCCTGGGGGAGT---ATTGCGGAGGAAGG     -
DH25.125      CCTGGGGGAGT---ATTGCGGAIGAAGG   +

DH25.46       CCTGGGGGAGT---ATTGCGGAGAAAGG   -
DH25.75    deaCCTGGGGGAGT---ATTGCGGAGGAAGG   +
DH25.8406meCCTGGGGGAGT---ATTGCGGAGGAAGG     +
DH25.126      CCTGGGGGAGT---ATTGCGGAGIAAGG   -
```

Fig. 5C

```
DH25.54      CCTGGAGGAGT---ATTGCGGAGGAAGG    ++
DH25.55      CCTGGAGGAGT---ATTGCGGGGGAAGG    ++
DH25.49      CCTGGGGGAGT---ATTGCGGTGGAAGG    +
DH25.50      CCTGGGGGAGT---ATTGCGGGGGAAGG    ++
DH25.51      CCTGGGGGAGT---ATTGCGGCGGAAGG    -
DH25.69   deaCCTGGGGGAGT---ATTGCGGAGGAAGG    +
DH25.7806meCCTGGGGGAGT---ATTGCGGAGGAAGG     +
DH25.86   deaCCTGGGGGAGT---ATTGCGGAGGAAGG    +
DH25.89   nebCCTGGGGGAGT---ATTGCGGAGGAAGG    ++
DH27.48      CCTGGTTGGAGT---ATTGCGGTTGGAAGG  -
```

Fig. 5D

```
DH25.61      CCTGGGGGCGT---ATTGCGGAGGAAGG    -
DH25.62      CCTGGGGGTGT---ATTGCGGAGGAAGG    -
DH25.63      CCTGGGGGGGT---ATTGCGGAGGAAGG    -
DH24.92      CCTGGGGG-GT---ATTGCGGAGGAAGG    -
DH25.85   deaCCTGGGGGAGT---ATTGCGGAGGAAGG   -
DH25.88   nebCCTGGGGGAGT---ATTGCGGAGGAAGG   +
```

Fig. 5E

```
DH25.64      CCTGGGGGAGT---ATTGCGGAGGCAGG    -
DH25.65      CCTGGGGGAGT---ATTGCGGAGGGAGG    -
DH25.66      CCTGGGGGAGT---ATTGCGGAGGTAGG    -
DH24.93      CCTGGGGGAGT---ATTGCGGAGG-AGG    +
DH24.94      CCAGGGGGAGT---ATTGCGGAGG-TGG    -
DH24.95      CGCGGGGGAGT---ATTGCGGAGG-GCG    -
DH25.87   deaCCTGGGGGAGT---ATTGCGGAGGAAGG   +/-
DH25.92   deaCGCGGGGGAGT---ATTGCGGAGGAGCG   -
DH25.90   nebCCTGGGGGAGT---ATTGCGGAGGAAGG   ++
DH25.94   nebCGCGGGGGAGT---ATTGCGGAGGAGCG   +
```

Fig. 5F

```
DH29.36      CCTGGGGGGGAGT---ATTGCGGGAGGGAAGG  ++
DH32.39      ATAGCGGAGGAAGGATACCTGGGGGAGTATAT  ++

DH15.99         CCTGGAGGAGTATAT
DH14.11         ATAGCGGAGGAAGG
DH20.155        ATTATAGCGGAGGAAGGTAT
DH21.82           ATACCTGGGGGAGTATATAAT
```

Fig. 5G

DH29.36
TRIPLE G-QUARTET STRUCTURE

DH32.39
ALTERNATE 5' & 3' ENDS

DH21.82 + DH20.155

DH27.48
TWO T MINOR GROOVE LOOP

DNA APTAMERS AND CATALYSTS THAT BIND ADENOSINE OR ADENOSINE-5'-PHOSPHATES AND METHODS FOR ISOLATION THEREOF

This invention was made in part with Government funding, and the Government therefore has certain rights in the invention.

BACKGROUND OF THE INVENTION

This invention relates to single-stranded ligand-binding DNA molecules and methods for the identification and isolation of these and catalytic DNA molecules.

ATP is an important substrate in biological reactions, and adenosine is a component of many biological cofactors. The isolation of receptors for ATP could be used in the design of molecules utilizing the stored energy in the adenyl phosphate bond to carry out desired catalytic activities.

SUMMARY OF THE INVENTION

In general, the invention concerns two methods: one for creating, identifying, and isolating single-stranded DNA molecules capable of binding adenosine or adenosine-5'-phosphates, such as ATP (termed "aptamers"); and a second for creating, identifying, and isolating single-stranded DNA molecules capable of both binding adenosine or an adenosine-5'-phosphate and catalyzing a reaction modifying the catalytic DNA (or another substrate) (termed "catalysts").

These methods entail sequential in vitro selections using pools of single-stranded DNA molecules of random sequence and isolation of those DNA molecules which are capable of binding the ligand (in this case, adenosine or an adenosine-5'-phosphate) and/or catalyzing the desired reaction. Isolated DNAs are then amplified using PCR. These rounds of selection and amplification may be repeated one or more times, after each round, the pool of molecules being enriched for those having the desired binding or catalytic activity. Although the number of desired molecules in the initial DNA pool may be exceedingly small, the sequential selection scheme overcomes this problem by repeatedly enriching for aptamers and catalysts of choice.

The pool of single-stranded DNAs employed in the invention are often referred to as "random DNAs" or "random sequences." These are general terms used to describe molecules or sequences which have one or more regions of "fully random sequence." Fully random sequence is sequence in which there is a roughly equal probability of each of A, T, C, and G being present at each position in the sequence. Of course, the limitations of some of the methods used to create nucleic acid molecules make it rather difficult to create fully random sequences in which the probability of each nucleotide occurring at each position is absolutely equal. Accordingly, sequences in which the probabilities are roughly equal are considered fully random sequences. In "partially random sequences" and "partially randomized sequences," rather than there being a 25% chance of each of A, T, C, and G being present at each position, there are unequal probabilities. For example, in a partially random sequence, there may be a 70% chance of A being present at a given position and a 10% chance of each of T, C, and G being present. Further, the probabilities can be the same or different at each position within the partially randomized region. Thus, a partially random sequence may include one or more positions at which the sequence is fully random and one or more positions at which the sequence is defined.

Such partially random sequences are particularly useful when one wishes to make variants of a known sequence. For example, if one knows that a particular 25 base sequence binds the selected ligand and that positions 5, 7, 8, and 9 are critical for binding, one could prepare a partially random version of the 25 base sequence in which the bases at positions 5, 7, 8, and 9 are the same as in the known ligand binding sequence, and the other positions are fully randomized. Alternatively, one could prepare a partially random sequence in which positions 5, 7, 8, and 9 are partially randomized, but with a strong bias towards the bases found at each position in the original molecule, with all of the other positions being fully randomized. This type of partially random sequence is desirable in pools of molecules from which DNA aptamers or catalytic DNAs are being selected. The sequence of any randomized region may be further randomized by mutagenesis during one or more amplification steps.

In addition to a random or partially random sequence, it may also be desirable to have one, or two, regions of "defined sequence." Defined sequence is sequence selected or known by the creator of the molecule. Such defined sequence regions are useful for isolating or PCR amplifying the nucleic acid because they are recognized by defined complementary primers. The defined primers can be used to isolate or amplify sequences having the corresponding defined sequences. The defined sequence regions preferably flank the random regions, but can less preferably be intermingled with the random regions. The defined regions can be of any desired length and are readily designed using knowledge in the art (see, for example, Ausubel et al., *Current Protocols in Molecular Biology*, Greene Publishing, New York, N.Y. (1994); Ehrlich, *PCR Technology*, Stockton Press, New York, N.Y. (1989); and Innis et al., *PCR Protocols, A Guide to Methods and Applications*, Academic Press, Inc., San Diego, Calif. (1990)).

In the first step, single-stranded DNA molecules capable of binding the ligands adenosine or adenosine-5'-phosphates are identified. Beginning with a pool of random DNAs, the method for isolating ligand-binding molecules involves contacting the pool of DNAs with the ligand under conditions which are favorable for binding, partitioning nucleic acids which have bound the ligand from those which have not, dissociating bound DNAs and ligand, amplifying the DNAs (e.g., using PCR) which were previously bound, and, if desired, repeating the steps of binding, partitioning, dissociating, and amplifying any desired number of times.

Several cycles of selection (binding, partitioning, dissociating, and amplifying) are desirable because after each round the pool is more enriched for ligand binding DNAs. One can perform additional cycles of selection until no substantial improvement in binding is observed. Of course, one can also perform far fewer cycles of selection.

In addition, one may mutagenize isolated DNA aptamers to isolate candidates exhibiting improved binding. For example, one may prepare degenerate pools of single-stranded DNAs based on a particular aptamer sequence, or one may first identify important binding regions in an aptamer (for example, by standard deletion analysis) and then prepare pools of candidate aptamers that include degenerate sequences at those important regions.

Useful aptamers may be partitioned using any standard affinity method. For example, affinity columns to which the ligand is attached may be utilized, and the ligand obtained by specific elution.

In many cases, sequencing of DNA aptamers isolated after one or more rounds of partitioning and amplification will reveal the presence of a number of different nucleic acid sequences. One or more of these sequences can be used in the pool of nucleic acids from which catalytic DNAs are isolated in the second method of the invention. Alternatively, the pool for the isolation of catalytic DNAs can be composed of one or more nucleic acids having sequences based on the sequences of the nucleic acids identified in the binding selection. For example, sequencing of the nucleic acids which bind the ligand may suggest one or more regions of consensus sequence, i.e., sequences which appear to be important for binding. The pool of molecules used for selection of catalytic molecules may then include nucleic acids whose sequence is based on this consensus sequence. One may also employ a partially randomized sequence based on the consensus sequence. This may permit the isolation of improved binding domains. It can also permit alterations of the binding domain which may be desirable for improved catalysis. Of course, as discussed above, the degree of randomization of the consensus sequence is generally quite low. The consensus sequence region, randomized or not, may be interspersed with and/or flanked by additional randomized regions. Thus, the sequences of the molecules in the pool of DNAs used in the catalysis selection step can differ from that of the molecule(s) identified in the ligand selection step as molecules capable of binding the desired ligand.

Those skilled in the art can readily identify ligand-binding consensus sequences by sequencing a number of ligand-binding DNAs and comparing their sequences. In some cases such sequencing and comparison will reveal the presence of a number of different ligand binding sequences. In these circumstances, one may identify a core sequence which is common to most or all sequences. This core sequence or variants thereof can be used as the starting point for the catalysis selection. By "variant" of a ligand binding sequence is meant a sequence created by partially randomizing a ligand binding sequence.

The size of the randomized regions employed should be adequate to provide a ligand binding site in the case of the binding selection step. Thus, the randomized region used in the initial binding selection preferably includes between 15 and 80 nucleotides, and preferably the isolated domain includes between 20 and 40 nucleotides. The randomized region or regions used for the catalysis selection step should be of sufficient length to provide a reasonable probability of being able to include catalytic activity.

The probability that any given DNA sequence of 30, 50, 100, or even 400 bases includes a region capable of binding a chosen ligand is very low. Similarly, the probability that a given DNA sequence which includes a region capable of binding a chosen ligand also has a region capable of catalyzing a reaction involving the chosen ligand is very low. Because of this, each of the two selection steps preferably begins with a pool of molecules which is large enough and random enough to include molecules which can bind the chosen ligand in the case of the binding selection and/or catalyze a reaction involving the chosen ligand in the case of the catalysis selection. Binding sites may occur at a frequency of $10^{-10}$ to $10^{-15}$ in random sequences. Thus, pool sizes are preferably greater than $10^{15}$ molecules.

The catalysis selection step involves identifying DNAs which catalyze a reaction involving the chosen ligand. The pool of molecules used at the outset of this selection step generally is composed of molecules having one or more defined or partially randomized sequences which are designed to bind to the chosen ligand ("ligand binding region") as well as a second random sequence region, preferably fully randomized which serves as the source of potentially catalytic sequences. The ligand binding region included in the molecules in this catalysis selection pool can have a sequence which is identical to an identified ligand binding sequence identified in the binding selection phase. Alternatively the sequence of this region can be based on the consensus sequence of a number of ligand binding regions identified in the first step. The region may also be a partially randomized sequenced based on either a particular ligand binding sequence or ligand binding consensus sequence. Of course, the molecules also preferably include one or more defined sequence regions which can bind isolation or amplification primers.

In order to identify molecules having catalytic activity there must be a means for partitioning those DNA molecules which have catalyzed a reaction modifying the DNA molecule (or a substrate attached to the DNA) from those which have not. The selection can be accomplished using affinity columns which will bind modified, but not unmodified molecules. Alternatively, one can employ an antibody which recognizes the modified, but not unmodified molecules. It is also possible to chemically convert modified, but not unmodified ligand, to a compound which will bind selectively to an affinity column or other selective binding material (e.g., an antibody).

In many cases the catalytic DNA will itself be chemically altered (modified) by the reaction it catalyzes. This alteration can then form the basis for selecting catalytic molecules.

In many cases it may be possible to alter such catalytic DNA molecules so that instead of being self-modifying they modify a second molecule.

It may be desirable to increase the stringency of a selection step in order to isolate more desirable molecules. The stringency of the binding selection step can be increased by decreasing ligand concentration. The stringency of the catalysis selection step can be increased by decreasing the ligand concentration or the reaction time.

One can covalently link a molecule to be modified to DNA so that catalytic DNA molecules can be isolated by isolating the modified molecule. For example, one might wish to find DNAs capable of oxidizing compound A. This might be accomplished by isolating DNA molecules capable of binding a redox co-factor (NAD, FAD, or NADP). A pool of random DNAs is then created which are capable of binding the cofactor. Compound A is then covalently attached to the DNA molecules in this pool and a selection is carried out which isolates molecules having the oxidized form of compound A. Methods for linking various compounds to DNA are well known to those skilled in the art and include the use of a thiophosphate group and the use of amines linked via a 5' phosphate.

Of course, in some cases a catalytic DNA which is capable of self-modification or modification of an attached substrate may also be able to perform the "trans" reaction. Such trans acting molecules modify a DNA other than themselves or modify the substrate even when it is not attached to the catalytic DNA.

In one aspect, therefore, the invention features a method for producing a single-stranded DNA molecule that binds adenosine or an adenosine-5'-phosphate (preferably, ATP). The method involves the steps of:

a) providing a population of DNA molecules each having a region of random sequence;

b) contacting the population with adenosine or an adenosine-5'-phosphate;

c) isolating a subpopulation of the population by partitioning DNA molecules in the population which specifically bind adenosine or adenosine-5'-phosphate from those which do not;

d) amplifying the subpopulation in vitro;

e) optionally repeating steps b–d for the amplified subpopulation; and f) obtaining from the amplified subpopulation a single-stranded DNA molecule capable of binding adenosine or an adenosine-5'-phosphate.

In another aspect, the invention features a single-stranded DNA molecule which binds adenosine or an adenosine-5'-phosphate (preferably, ATP). In preferred embodiments, the DNA molecule includes a guanosine-rich region (preferably, a G-quartet); the DNA molecule includes adenosine residues adjacent the guanosine-rich region (preferably, between 1 and 3 nucleotides from, and more preferably, immediately contiguous to, the terminal guanosine of that guanosine-rich region); the DNA molecule includes one or more base-paired nucleic acids adjacent each guanosine-rich region (preferably, the base-paired nucleic acid most proximal to the guanosine-rich region is within 0–5 residues, and more preferably, within 0–1 residue of proximal-most terminal guanosine); and the base-paired nucleic acids form stem or stem-loop structures.

In a third aspect, the invention features a method for producing a catalytic DNA molecule capable of binding a first ligand and catalyzing a chemical reaction modifying the DNA molecule. The method involves the steps of:

a) providing a first population of DNA molecules each having a first region of random sequence;

b) contacting the first population of DNA molecules with the first ligand;

c) isolating a first ligand-binding subpopulation of the first population of DNA molecules by partitioning DNA molecules in the first population which specifically bind the first ligand from those which do not;

d) amplifying the first ligand-binding subpopulation in vitro;

e) identifying a first ligand binding sequence;

f) preparing a second population of DNA molecules each of the DNA molecules including the first ligand binding sequence and a second region of random sequence;

g) contacting the second population of DNA molecules with a second ligand capable of binding the first ligand binding sequence; and h) isolating a subpopulation of the catalytic DNA molecules from the second population of DNA molecules by partitioning DNA molecules which have been modified in step g) from those which have not been modified.

In preferred embodiments, the first ligand is ATP; the second ligand serves as a substrate for the chemical reaction; and the catalytic DNA molecule transfers a phosphate from a nucleotide triphosphate to a catalytic DNA molecule. In an alternative method, the catalytic DNA modifies a substrate other than the catalytic DNA molecule or modifies a substrate attached to the catalytic DNA.

By "adenosine-5'-phosphate" is meant adenosine monophosphate (AMP), adenosine diphosphate (ADP), and adenosine triphosphate (ATP).

By "partitioning" is meant separating molecules of interest from undesirable molecules in a particular sample. This may be accomplished by any standard separation technique, for example, affinity column chromatography. Preferably, the molecule or molecules of interest are separated from undesirable molecules by at least 60%, more preferably 75%, and most preferably at least 90%.

By "amplifying" is meant duplicating one or more times. Preferably, amplification is carried out by standard PCR techniques as described herein.

By "guanosine-rich region" is meant a stretch of nucleic acids that begins and ends with guanosine and includes at least 65%, and more preferably between 80–100% guanosine residues. In addition, this region is preferably between 5–31, more preferably between 5–7, and most preferably 7 nucleic acids in length.

By "G-quartet" is meant a guanosine-rich region that is capable of forming the structures described herein and in Saenger, Principles of Nucleic Acid Structure, Springer-Verlag, New York (1984). Although molecules including a single G-quartet are useful in the invention, preferable DNA aptamers include two or more G-quartets. G-quartets according to the invention preferably include guanosine at all critical positions, but may include residues other than guanosine at certain positions; acceptable substitutions are those which do not abolish ligand binding. Examples of such substitutions are described herein.

By "stem" structure is meant any stretch of intramolecular base-paired nucleic acid sequence, regardless of length. By "stem-loop" structure is meant any stretch of intramolecular base-paired nucleic acid sequence that includes an internal region of unpaired sequence (i.e., the loop), again regardless of length.

Single-stranded DNA molecules according to the invention may be a single oligonucleotide or, as described herein, may be a combination of two or more oligonucleotides that fold into a workable aptamer structure.

Referring to FIG. 7, the "L1" and "L3" nucleotides are preferably both purine residues. The "P1" and "P2" regions must be at least one nucleotide pair in length, but may vary up to any length and preferably form stem or stem-loop structures, more preferably, forming one or more regions of double helical structure. Most preferably, P1 is three nucleotide pairs in length, and P2 is two nucleotide pairs in length. The adenosine residues ("invariant A's") are preferably immediately contiguous to a guanosine-rich region (as shown in FIG. 7), but may be either 5' or 3' to those regions.

Desirable single-stranded DNA molecules of the invention have at least 70%, preferably at least 80%, more preferably at least 90% sequence identity to the core binding regions of the sequences listed in FIG. 4A or FIG. 5A. The core binding region is the minimal sequence required for binding activity. This sequence is determined using standard deletion analysis and/or site-directed mutagenesis as described herein.

The DNA molecules of the invention provide significant advantages over ligand-binding and catalytic RNAs in terms of both stability and cost of synthesis.

Other features and advantages of the invention will be apparent from the following description of the preferred embodiments thereof, and from the claims.

DETAILED DESCRIPTION

The drawings will first be described.

DESCRIPTION OF THE DRAWINGS

FIG. 1A shows the hydrogen bonding relationship between the four guanosines of a quartet. FIG. 1B shows a representation of a thrombin aptamer (Bock et al., Nature 355: 564–566 (1992), illustrating the two stacked G-quartets.

FIG. 3A shows the column binding profile of the round 8 pool and clone 4. Fraction of loaded DNA eluted is plotted as a function of column volumes of buffer wash; ATP was added to the wash buffer after 5 column volumes. Closed boxes: 8th round pool; open circles: clone 4. FIG. 3B shows the column binding profile of flowthrough and specifically eluted fractions of clone 4 DNA. Clone 4 DNA was chromatographed as above, and the 1st wash fraction and the pooled ATP eluate fractions were precipitated, desalted and residual ATP removed by Sephadex spin column chromatography, heat denatured and renatured in column buffer. This DNA was then placed on a new ATP column and the profile is shown. Open circles: clone 4 flowthrough; closed boxes: clone 4 ATP eluate. In each case the data point of the 9th column volume is that which was remaining on the column after all washes.

FIG. 4A is a list of sequences of 45 clones (SEQ ID NOS: 1–45) from the 4th round selection. Dark shading: conserved guanosine rich areas. Medium shading: invariant adenosine residues.: P1 and P1' (light shading) and P2 and P2' (open boxes) are complementary regions that show extensive covariation.

FIG. 5A–G are sequences synthesized to test importance of specific bases or functional groups of the aptamer. In all cases the outlined base(s) represents the change being made. Binding efficiency of the aptamer is denoted as a ++=95–80% retention on the column, +=79%–20% retention on the column, +/−=19–1% retention on the column, and −=no column retention. FIG. 5A shows parental or reference sequence DH25.42 (SEQ ID NO:46), derived from the sequence of clone 16, the only clone represented twice in the selected pool. FIG. 5B shows sequences (SEQ ID NOS:47–60) tested for optimal stem lengths. FIG. 5C shows sequences (SEQ ID NOS:61–92) with changes in highly conserved guanosine pairs. In sequences preceded by dea or O-6me the substitutions were 7-deaza-2'-deoxyguanosine and O-6-methyl-2'-deoxyguanosine respectively; I represents inosine. FIG. 5D (SEQ ID NOS:93–102) shows changes in L1 and L3, the single bases bridging the proposed minor grooves of the G-quartet. FIG. 5E (SEQ ID Nos: 103–108) shows changes of invariant adenosine A9. Sequences preceded by dea or neb are 7-deaza-2'-deoxyadenosine or 2'-deoxynebularine (purine riboside) substitutions respectively. FIG. 5F (SEQ ID NOS:109–118) shows changes of invariant adenosine A22. FIG. 5G (SEQ ID NOS: 119–124) shows sequences of engineered aptamers and oligonucleotides used in the heterodimer assembly studies.

FIG. 8A (SEQ ID No: 126) is the predicted structure of DH29.36, with three stacked G-quartets. FIG. 8B (SEQ ID NO: 127) is the predicted structure of DH32.29. Original loop L2 has been deleted, creating new 5' to 3' ends, while original 5' and 3' ends have been joined by a new loop. FIG. 8C (SEQ ID NO: 128) is the predicted structure formed by assembly of oligonucleotides DH21.82 and DH20.155. FIG. 8D (SEQ ID NO: 129) shows oligonucleotide DH27.48, showing change of each single base minor groove bridge to the TT bridge employed by thrombin aptamer.

The isolation and characterization of a DNA aptamer that binds adenosine and ATP in solution is now described. Covariation, nucleotide analog substitution, and redesigned aptamers indicate that the structure of this aptamer in solution consists of two small Watson-Crick helices and two G-quartets.

Figure 1A:
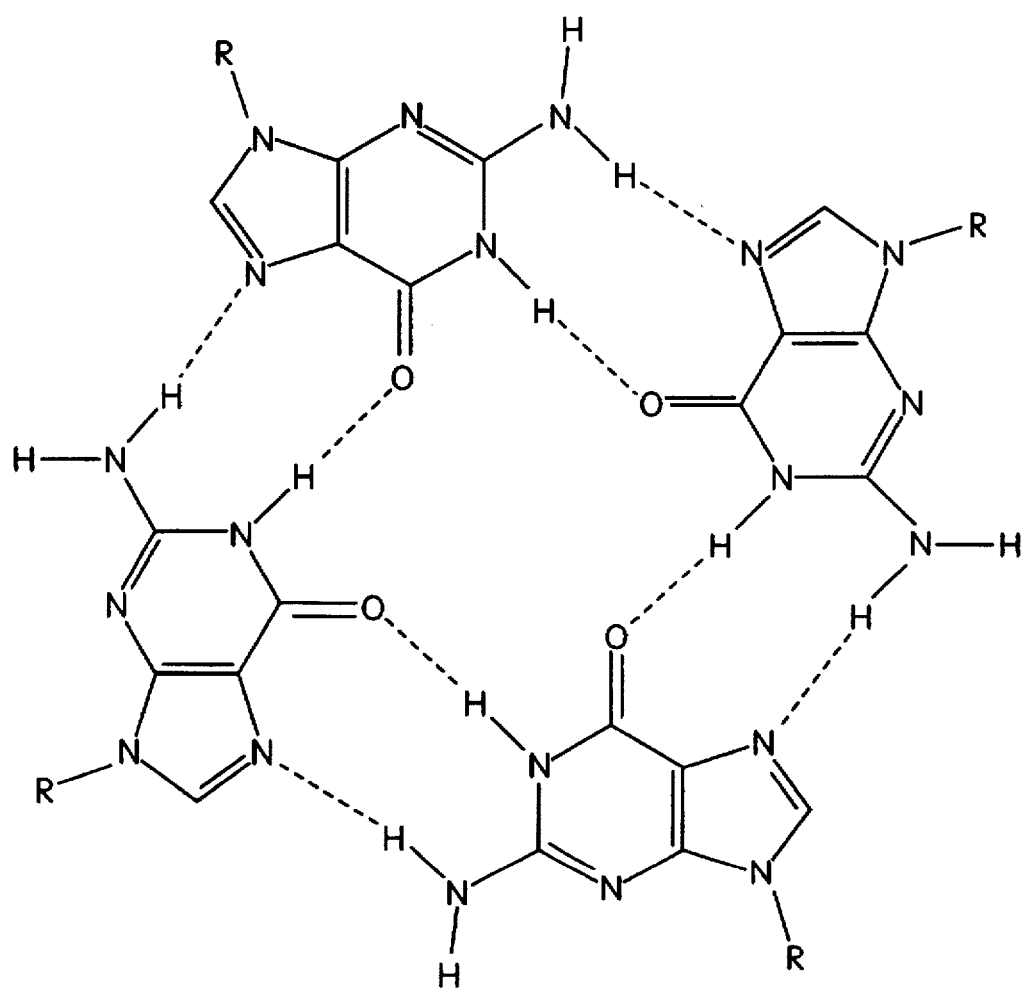
FIG. 1A and 1B are schematic representations of G-quartets.
Figure 1B:
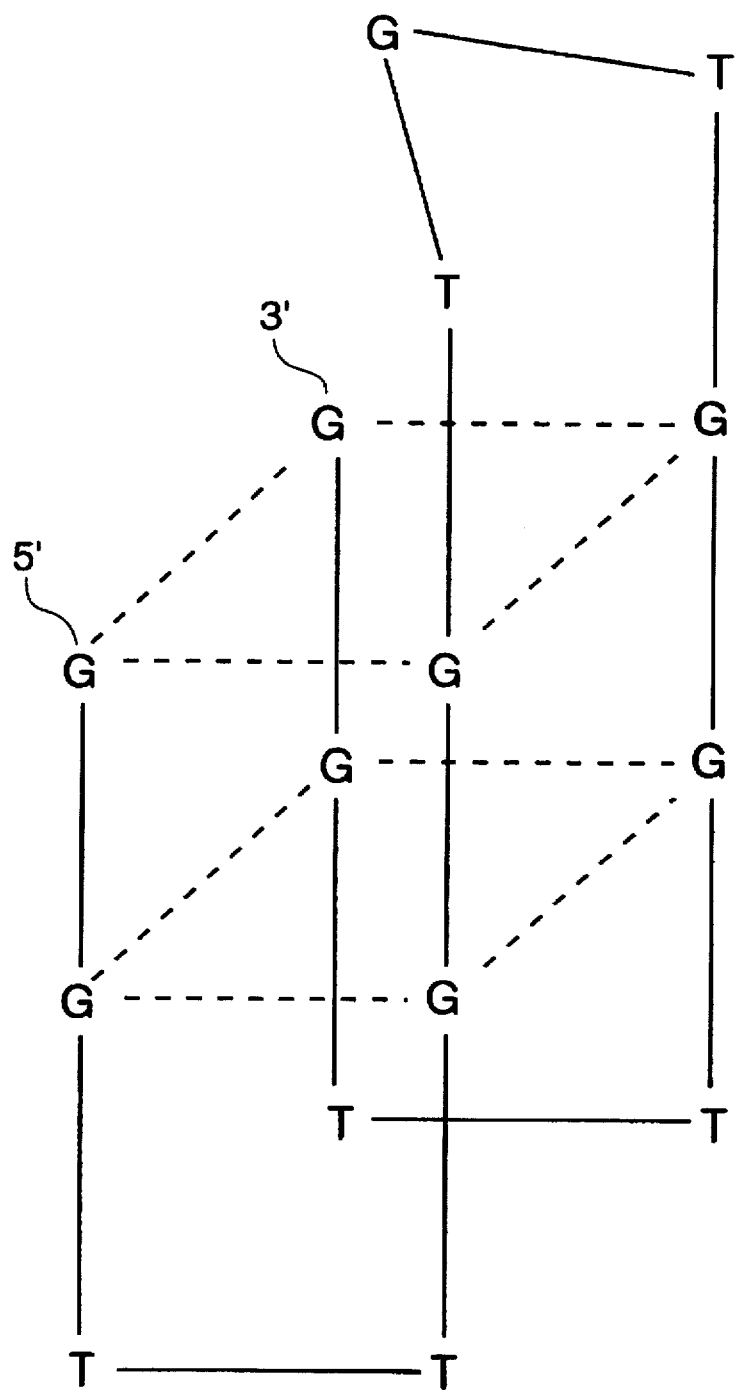

The G-quartet structure is very stable and highly symmetric. Four guanosines assemble by hydrogen bonding between the Hoogsteen and Watson-Crick faces of adjacent guanosines. Two to four G-quartets can stack on each other to form aggregates that are stabilized by monovalent cations such as $Na^+$ and $K^+$ which are thought to interact with the carbonyl oxygens of the guanosines (for review see Saenger, *Principles of Nucleic Acid Structure* Springer-Verlag, New York, (1984); Sen et al., *Methods in Enzymology* 211:191–199, (1992) (FIG. 1A).

A number of variants of this basic structure exist, which differ in symmetry, the orientation of adjacent strands, and the glycosidic configuration about the quartets. In the simplest form, four different strands of DNA (Sen et al., *Nature* 334:364–366, (1988); Sen et al., *Nature* 344:410–414, (1990)) or RNA (Kim et al., *Nature* 351:331–332, (1991)) each contribute a single guanosine to each quartet. In this configuration the four strands of DNA are parallel and the guanosines that comprise the quartet are all anti in configuration.

G-quartets can also arise from two strands of DNA that assemble such that each strand contributes two guanosines to each quartet (Sundquist et al., *Nature* 342:825–829, (1989)). This dimerization can yield a variety of different structures. One such structure, which can be viewed as a dimer of hairpin loops, has been characterized by X-ray crystallography; in this structure all adjacent strands are anti-parallel, and the guanosines are syn-anti-syn-anti around the quartet (Kang et al., *Nature* 356:126–131, (1992)). This type of hairpin interaction can also take place in an intrastrand association (Williamson et al., *Cell* 59:871–880, (1989)). In a second form of dimer, adjacent strands are from different DNA molecules and are alternately parallel and anti-parallel (Smith et al., *Nature* 356:164–168, (1992); Smith et al., *Biochemistry* 32:8682–8692, (1993)). In this structure the guanosines are syn-syn-anti-anti around the quartet, and the stack of quartets has minor, intermediate and major grooves.

Stacked G-quartets form a very stable structure that is apparently able to tolerate a wide variation in the details of backbone structure, including strand orientations, glycosidic conformations and connecting loop lengths.

Selection of Single-Stranded DNA Molecules that Bind ATP

Figure 2A:
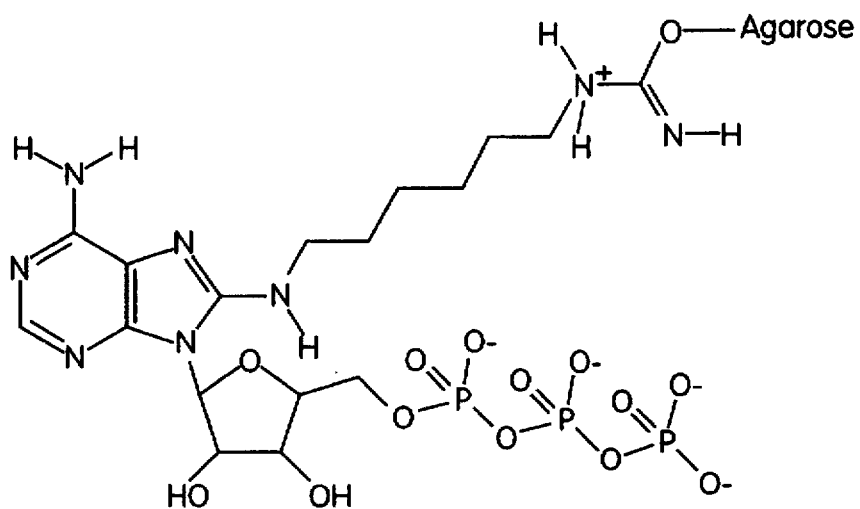
FIG. 2A is a schematic drawing of a matrix used for affinity selection. The ATP is linked at the C8 of the purine ring through a 9 atom spacer to agarose.
Figure 2B:
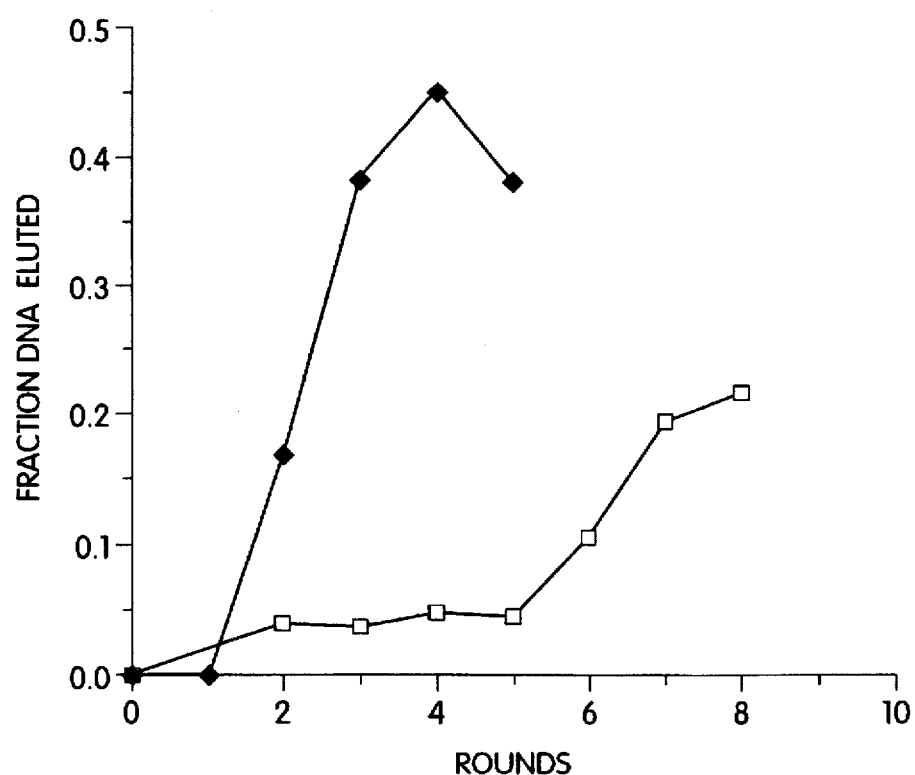
FIG. 2B is a graph showing the fraction of loaded DNA specifically eluted from the column vs. selection round. Open boxes: original selection from the random sequence pool. Fraction of DNA remaining on the ATP column after washing with five column volumes of buffer, and eluted with three column volumes of buffer plus ATP. Data point at 8th round represents polyacrylamide gel purified DNA, non gel-purified DNA showed ≅17% retention on the column. Closed diamonds: secondary selection from the mutagenized sequence pool. Fraction of DNA remaining on the ATP column after washing with ten column volumes of buffer, and eluted with three column volumes of buffer plus ATP.

DNA sequences that bind ATP were isolated by repeated rounds of enrichment by affinity chromatography on ATP-agarose followed by PCR amplification and single-strand synthesis. The initial population of single-stranded random sequence DNA molecules was generated by six cycles of 5' primer extension on a pool of $\cong 2 * 10^{14}$ PCR-amplified dsDNA molecules (Bartel et al., *Science* 261:1411, (1993)) consisting of 72 random nucleotides flanked by 20 nucleotide primer binding sites. Approximately 150 µg of the single stranded DNA pool was used for the first round of selection, corresponding to an average of 10 copies of each sequence. The DNA, after equilibration in column buffer, was loaded onto a 1 ml column of cross-linked agarose containing 1–3 mM ATP linked at C8 to the matrix via a linker (FIG. 2A). Unbound or weakly bound DNA was washed off of the column with five column volumes of buffer. DNA that specifically bound ATP in solution was eluted by washing the column with three column volumes of buffer containing 3 mMATP. The DNA in the first two column volumes was concentrated, amplified by PCR, and a new enriched population of single-stranded DNAs was generated by primer extension as above. After 7 rounds of selection, $\cong 18\%$ of the input DNA bound to the column and was specifically eluted with ATP (FIG. 2B). This fraction increased to 21% at the 8th round. It is possible that this apparent plateau at $\cong 20\%$ binding is due to contamination of the single-stranded DNA with a substantial fraction of double-stranded DNA, or misfolded single-stranded DNA.

Figure 3A:
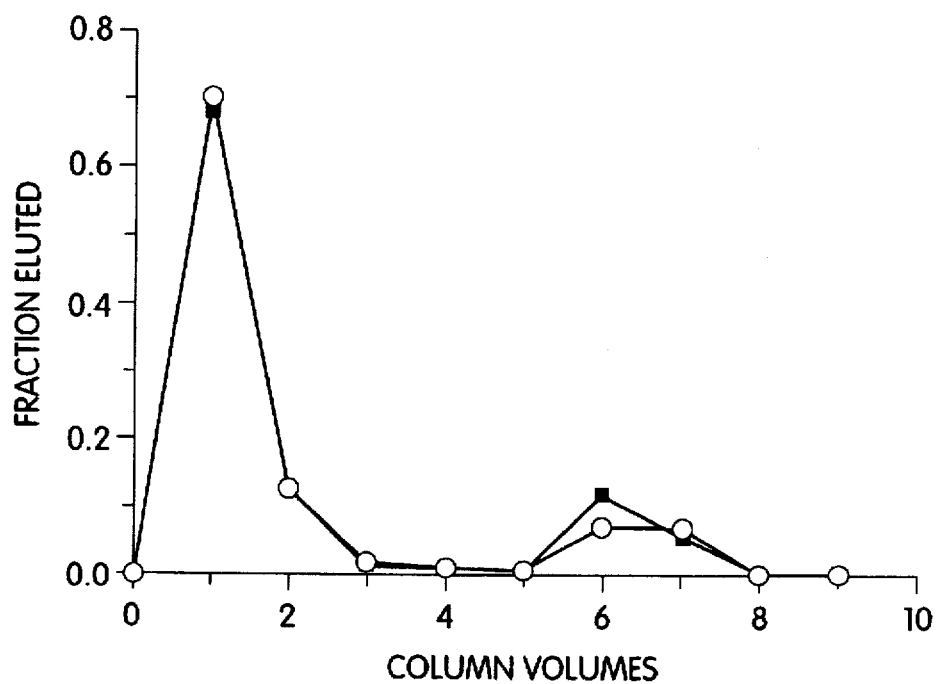
FIG. 3A and 3B are graphs showing elution profiles of selected DNAs.
Figure 3B:
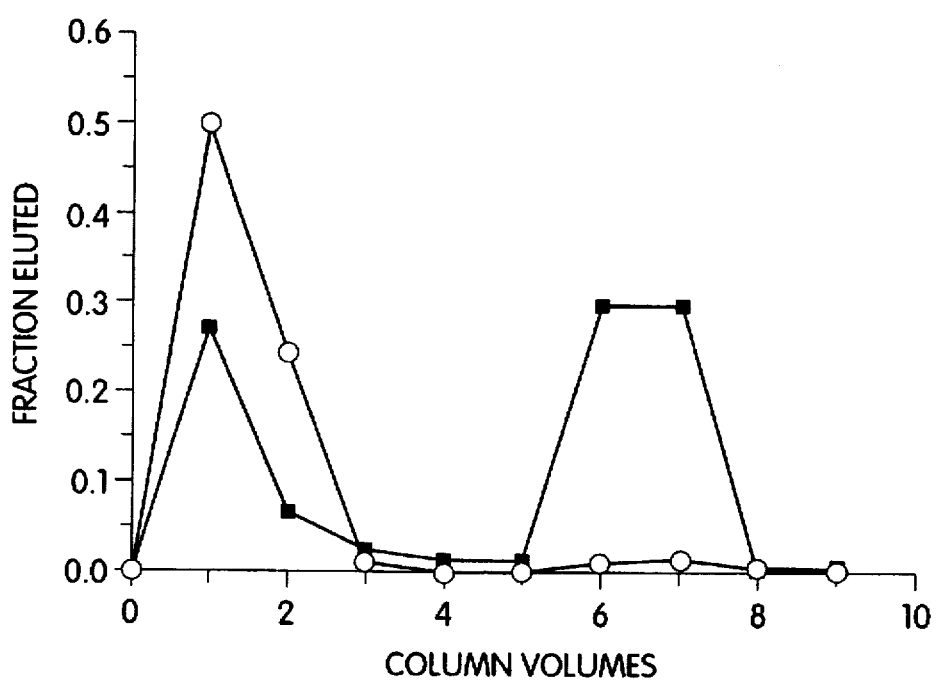

The round 8 DNA was cloned and 17 clones were sequenced. All of these clones had different sequences and appeared to be of independent origin. Single-stranded DNA was generated from two clones and was found to bind to the ATP-agarose column as well as the round 8 pool ($\cong 20\%$) (FIG. 3A). One of these clones (clone 4) was chosen for further analysis. The low fraction bound does not seem to be due to a large fraction of misfolded DNA, as very little flowthrough DNA ($\cong 3\%$) binds upon retesting, whereas specifically eluted DNA does bind efficiently ($\cong 60\%$) when retested (FIG. 3B). The presence of complementary strand DNA may explain these results. A series of synthetic oligonucleotides were made, covering progressively shorter portions of the clone 4 sequence. These oligonucleotides were assayed for ATP binding and the ATP-binding domain was localized to a 42 nucleotide sequence contained completely within the originally random region of the clone 4 sequence. The 42 nucleotide sequence bound at least as well as the full length clone.

Conserved and Invariant Bases with ATP-Binding Domain

In order to further define the bases that were critical for ATP-binding activity, we prepared a highly degenerate pool of sequences based upon the 42-nt active sequence, selected active sequence variants from the pool in a secondary selection, and then aligned and compared the sequences of these variants. A synthetic oligonucleotide consisting of the 42 nucleotide sequence mutagenized to an extent of $\cong 30\%$, flanked by the same primer binding sites as used before, was used as template for PCR amplification and subsequent single-stranded DNA synthesis. After 4 rounds of selection and amplification carried out as described above, $\cong 45\%$ of the DNA bound to the ATP-agarose column and was specifically eluted with ATP (FIG. 2B). No further enrichment was obtained with additional rounds of selection. PCR amplified DNA from round 4 was cloned and 45 clones were sequenced (FIG. 4A). Of the 45 sequences (SEQ ID NOS:), 44 were unique and one, clone 16, was present twice.

Figure 4B:
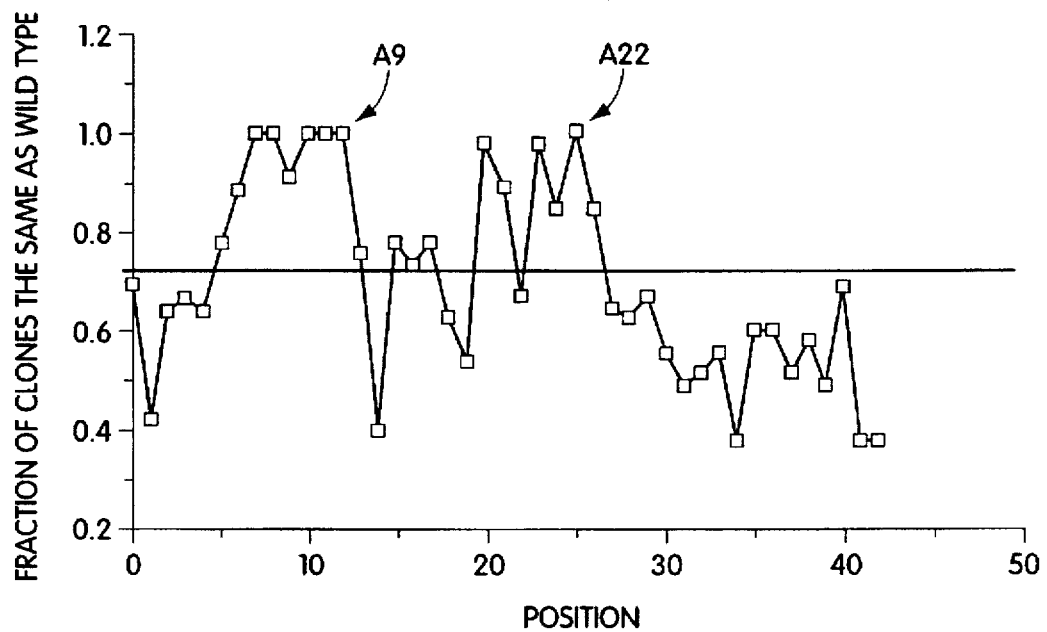
FIG. 4B is a graphic representation of sequence conservation after selection from the mutagenized pool. Percent conservation is based on 45 clones shown above.

Alignment of these sequences (FIG. 4A (SEQ ID NO: 1–45)) revealed two distinct regions of conservation (FIG. 4B), flanked by apparently non-conserved sequences. Each conserved region was 6 bases long, was highly guanosine-rich, and ended in a single invariant adenosine residue. We also observed two areas of covariation in the aligned sequences: one immediately inside the conserved G-rich segments, and a second immediately flanking the G-rich regions (FIG. 4A, Table 1).

TABLE 1

| Mutations in proposed stems conserving base pairing | | | |
|---|---|---|---|
| Wild type | Watson/Crick | G-T | Other |
| $C_1$–$G_{25}$ 24 | 11 | 1 | 9 |
| $C_2$–$G_{24}$ 29 | 8 | 5 | 3 |
| $T_3$–$A_{23}$ 37 | 4 | 3 | 1 |
| $G_{10}$–$C_{16}$ 28 | 8 | 3 | 6 |
| $T_{11}$–$G_{15}$ 12 | 19 | 1 | 13 |

Covariation at positions proposed to base-pair. The number of mutant clones out of 45 in each class is shown. In many of the clones the P1 stem was longer than three base pairs.

To see if the conserved and covarying sequences were sufficient for ATP-binding, a 25 base oligonucleotide (DH25.42; FIG. 5A SEQ ID NOS:47–60 ) that contained only these regions was synthesized. When this oligonucleotide was assayed for ATP binding, greater then 90% of the DNA remained on the ATP-agarose column after washing with ten column volumes of buffer, and was specifically eluted by ATP.

Specificity of the Ligand/Aptamer Interaction

The minimal ATP aptamer was used to obtain a qualitative view of the specificity of the ligand-aptamer interaction by assessing the ability of various ATP analogs to elute bound aptamer from an ATP-agarose column (FIG. 9A–C, FIG. 10). These experiments indicate that N7, N6, and N1 of the adenine moiety of ATP are important for interaction with the aptamer. Substitution or methylation of these positions prevents elution in 3 column volumes of 1.5 mM analog. In contrast, substitutions at C8 did not affect binding, consistent with the fact that the initial selection was for binding to ATP linked to the matrix through C8. Methylation of either C2 or N3 did not prevent aptamer binding. Similar experiments provide evidence for interactions between the aptamer and the ribose moiety of ATP. Removal of the 3'hydroxyl decreased binding, whereas loss of the 2'hydroxyl had no effect. However, deletion of both the 2' and the 5' hydroxyls of adenosine resulted in a partial loss of binding, suggesting the possibility of an interaction with O5'. The ligand aptamer interaction is steroselective with respect to the glycosidic bond, since 9-α-ribofuranosyladenine did not elute bound aptamer from the ATP-agarose column.

Although quantitative binding data from column elution experiments is imprecise, an estimate of adenosine affinity in solution was obtained by ultrafiltration experiments (Jenison et al., *Science* 263:1425–1429, (1994)). These experiments indicated that the $K_d$ for adenosine in solution was 6±3 μM.

Proposed Structure

Figure 7:
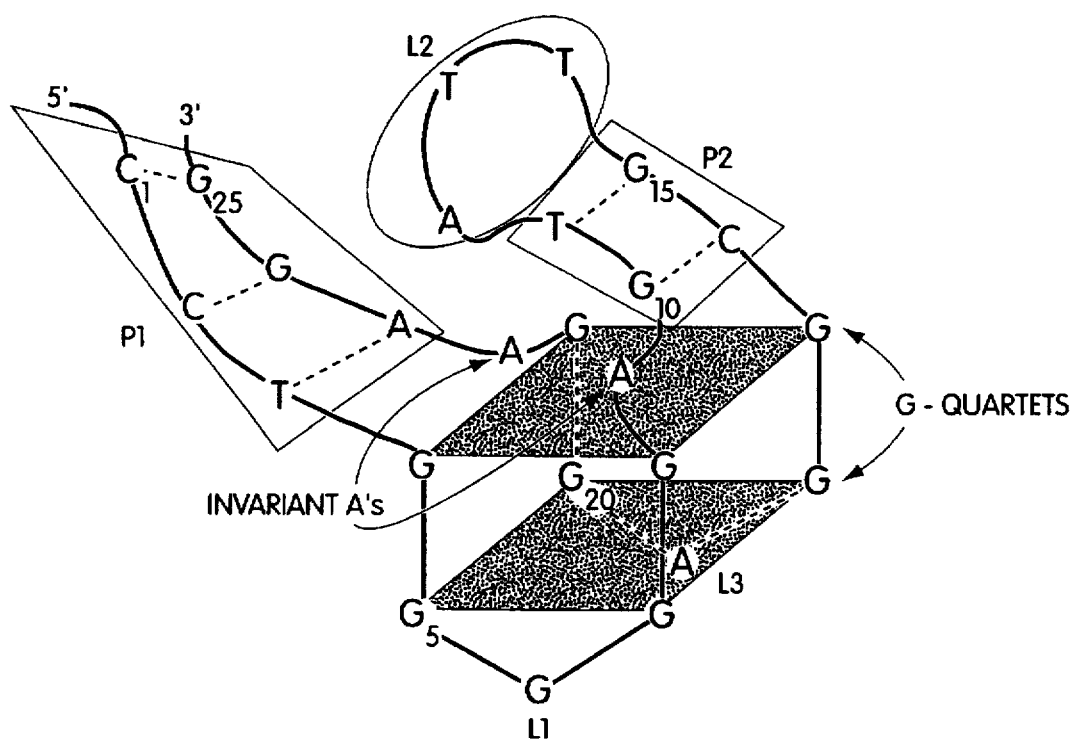
FIG. 7 (SEQ ID NO: 125) is a model of the structure of ATP aptamer. Base-paired stems are labeled P1 and P2, single base lower loops are L1 and L3; loop closing stem P2 is L2. Two stacked G-quartets act as a platform for two invariant adenosine residues proposed to stack in between upper quartet and stems P1 and P2. The proposed binding site for ATP is above the upper quartet and between the invariant adenosines. This representation is not meant to suggest the exact orientation of any residue.

A reasonable hypothesis for the structure of the DNA-ATP aptamer can be made based on the sequence comparison data (FIG. 7). The covariation data indicates that bases C1-G25, C2-G24, and T3-A23 are base-paired and are therefore likely to form a short region of double-helix (P1). Similarly, G10-C16, and T11-G15 are base-paired and form another short duplex (P2) closed by a three base loop (L2). The two G-rich regions can be viewed as four GG doublets, and are consistent with the formation of two stacked G-quartets, as seen in the thrombin aptamer (Bock et al., *Nature* 355:564–566, (1992)). However, in our model the loops below the bottom G-quartet (L1 and L3) consist of a single nucleotide (A or G) rather than two Ts as in the thrombin aptamer. The highly conserved adenosines, A9 and A22, are stacked between the top G-quartet and the stems P1 and P2.

Length and Sequence Effects in the Base-Paired Stems

A series of oligonucleotides was synthesized (FIG. 5B SEQ ID NOS:47–60) to determine the minimal and optimal length of each base-paired stem. These experiments indicated that a P1 stem of one base-pair was sufficient to detect ligand interaction on the ATP column, but that three base-pairs or more were required for optimal binding. A single base-pair P2 stem retains some binding activity, but two base pairs are optimal for binding. Increasing the length of stem P2 to three base-pairs results in an approximately two-fold decrease in column binding.

Experiments in which the sequences in the P1 and P2 regions were changed, but base-pairing potential was retained, strongly support the hypothesis that these regions of the aptamer are interacting to form small double helix regions. There is no clear indication that a strong sequence preference exists in either of these regions.

Substitution in the G-Quartet Regions

Figure 6:
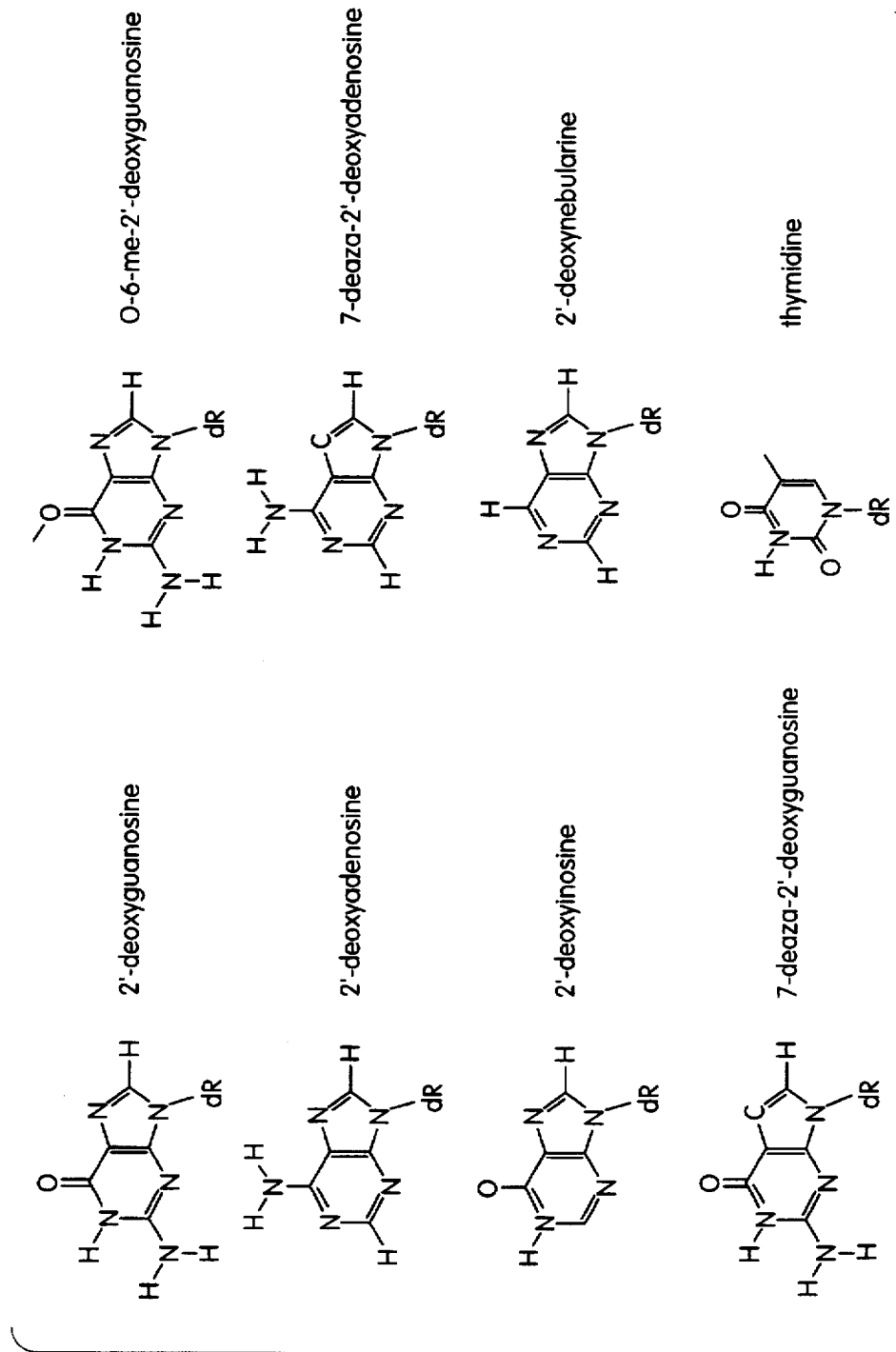
FIG. 6 is a series of schematic drawings showing the analogs of deoxyadenosine and deoxyguanosine that were used for the substitutions at each of the conserved adenosine residues and the conserved guanosine residues.

In our model, eight highly conserved Gs (four GG pairs) assemble to form two stacked G-quartets. To examine in greater detail the contribution of each of these eight residues to the functional aptamer structure, 32 oligonucleotides (FIG. 5C SEQ ID NOS:61–92) were made with single substitutions of 2'-deoxyadenosine, 2'-deoxyinosine, 7-deaza-2'-deoxyguanosine, and O-6-methyl-2'-deoxyguanosine at each of these positions (FIG. 6). All of the substitutions disrupt hydrogen bonds known to exist in G-quartets.

Substitution of 2'-deoxyadenosine would be expected to lead to loss of at least two hydrogen bonds from a quartet. At 6 of the 8 positions, a G to A change completely eliminated binding in the column assay. At the remaining two positions, corresponding to the first GG pair, a G to A substitution in the putative top quartet G had little effect and a G to A substitution in the putative bottom quartet G decreased but did not eliminate binding. G to T changes at these positions eliminated binding to the ATP column. These results are consistent with the highly conserved nature of the GG pairs seen in the secondary selection from the mutagenized pool.

A G to 2'-deoxyinosine substitution should be less disruptive, resulting in loss of one hydrogen bond, with minimal structural distortion. 2'-Deoxyinosine substitution reduced but did not eliminate binding at five positions, and eliminated binding to the column at the remaining three positions (FIG. 5C). These three critical positions were all in the putative top quartet. It is possible that the N2 amino groups of G4, G8, and G21 play a role above and beyond G-quartet formation, either directly interacting with ligand or stabilizing the aptamer structure through some tertiary interaction.

Substitution with 7-deaza-2'-deoxyguanosine should also lead to loss of one hydrogen bond, but with the potential for greater distortion due to a hydrogen-hydrogen steric clash. O-6-methyl-2'-deoxyguanosine substitution would also disrupt one hydrogen bond in a G-quartet, but would cause even greater distortion due to the bulky methyl group being introduced into the central region of the quartet. Both of these substitutions reduced binding six positions, and eliminated binding at two positions on the lower quartet.

Taken together, these data suggest that N7, O6 and N2 of the conserved guanosine residues play an important role in aptamer structure and/or ligand binding, and are consistent with the assembly of these G residues into G-quartets.

Tests of Proposed Secondary Structure

Figure 8A:
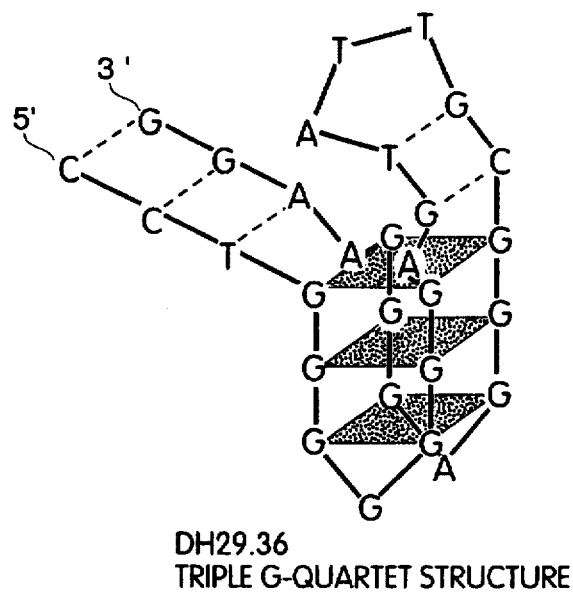
FIG. 8A–D are schematic diagrams of modified aptamer structures. Primary sequences are from FIG. 5.
Figure 8B:
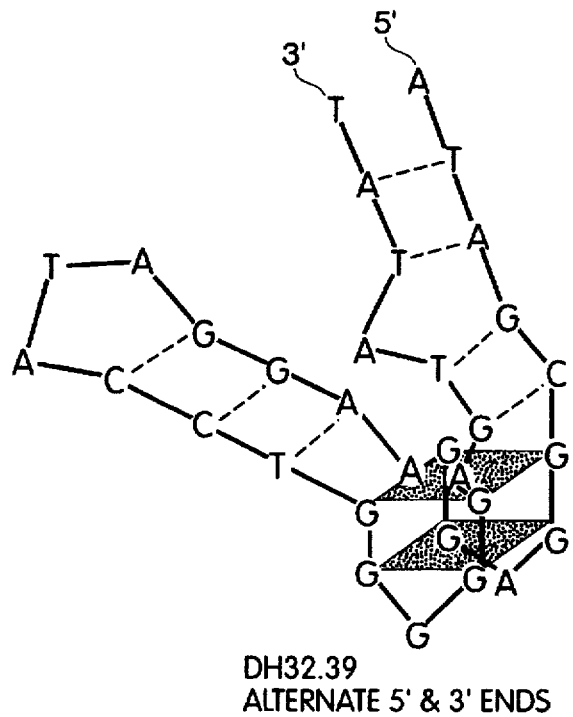

Two molecules which greatly altered the sequence of the aptamer were synthesized (FIG. 5G SEQ ID NOS:119–124; FIG. 8A & B (SEQ ID NOS:125–127)) to provide independent tests of the proposed secondary structure. In the first test, the sequence was changed so that it would fold into a structure with three G-quartets instead of the original two quartets. To do this, each GG pair was changed to a GGG triplet. This altered sequence binds ATP-agarose as well as the parental two-quartet sequence, providing strong evidence in favor of a folded G quartet structure.

In a second test, the P1 stem was changed into a stem-loop and the P2 stem-loop was changed into stem. This results in a permuted sequence in which the original 5' and 3' ends are joined with the three base loop and the proposed loop closing P2 is opened to create new 5' and 3' ends. In addition, P2 was extended by 3 additional base-pairs following a single unpaired adenosine (A12). This molecule has a very different primary sequence, but can be folded into nearly the same secondary structure as the parental aptamer; the altered sequence binds ATP-agarose as well as the parental sequence. Interestingly, removal of the extra-helical adenosine residue results in a partial loss of binding activity, supporting a role for A12 in aptamer structure and/or ligand binding (see below).

Figure 8C:
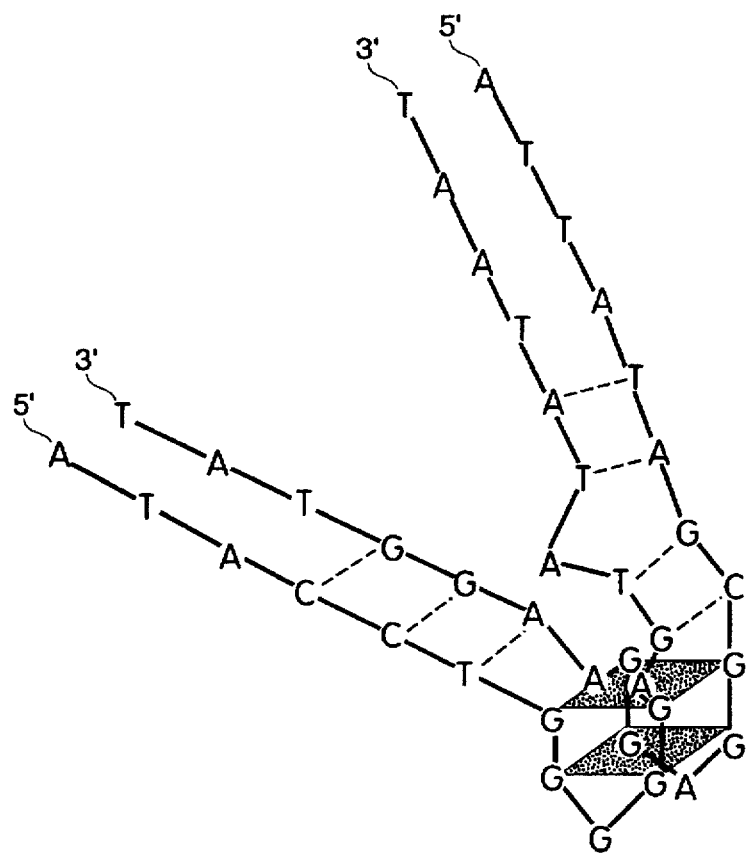

A third test of the proposed secondary structure involved the assembly of the complete structure from two oligonucleotides (FIG. 5G SEQ ID NOS:119–124 ; FIG. 8C SEQ ID NO:128). The aptamer structure was divided in two by simply removing L2, the loop that closes the P2 stem. To compensate for the resulting loss in stability, the P1 pairing was extended to 6 base-pairs, and P2 was extended to two base-pairs plus an additional six base-pairs after the unpaired adenosine. Neither of these oligonucelotides alone bound ATP, but when annealed together, the resulting heterodimer was able to bind to the ATP-agarose column, and was specifically eluted with ATP. Oligonucleotides that would pair to make shorter P1 and P2 stems bound more weakly.

Connecting Loops

Figure 8D:
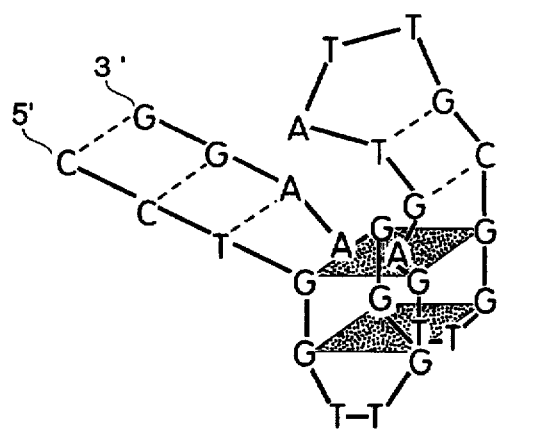
Figure 9A:
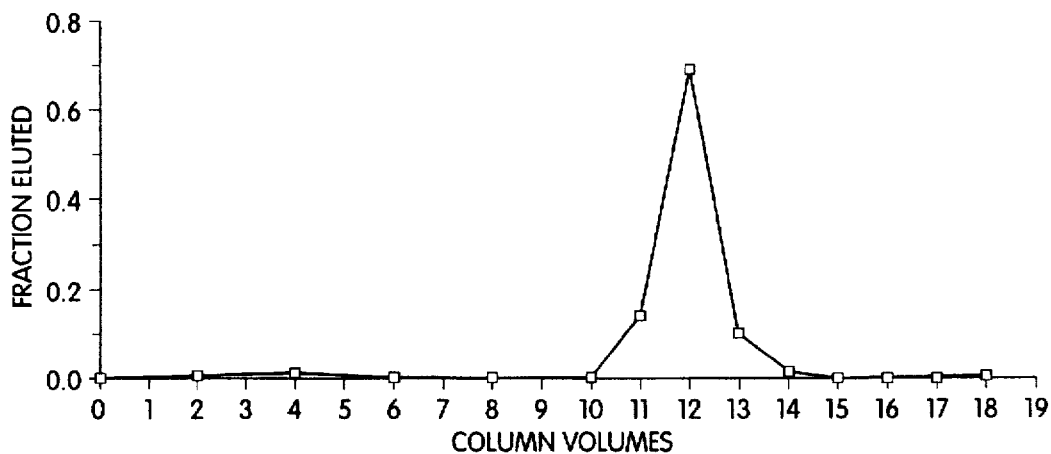
FIG. 9A–C are graphs of exemplary elution profiles with analogs of ATP. DNA was loaded onto an ATP-agarose affinity column and washed with 10 column volumes of wash buffer. Bound DNA was then eluted with 3 column volumes of wash buffer containing 1.5 mM analog, then washed with 2 more column volumes of wash buffer; remaining DNA was then eluted in 3 column volumes of wash buffer containing 1.5 mM ATP. Data point at column volume 19 is that remaining on the column after all washes. Elution profiles with 9A. adenosine, 9B. 3-methyl adenine, and 9C. purine riboside.
Figure 9B:
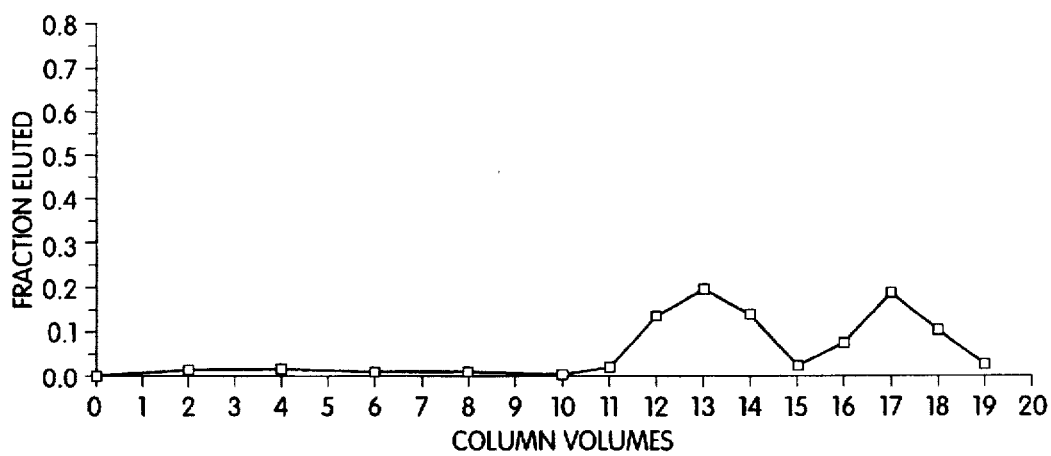
Figure 9C:
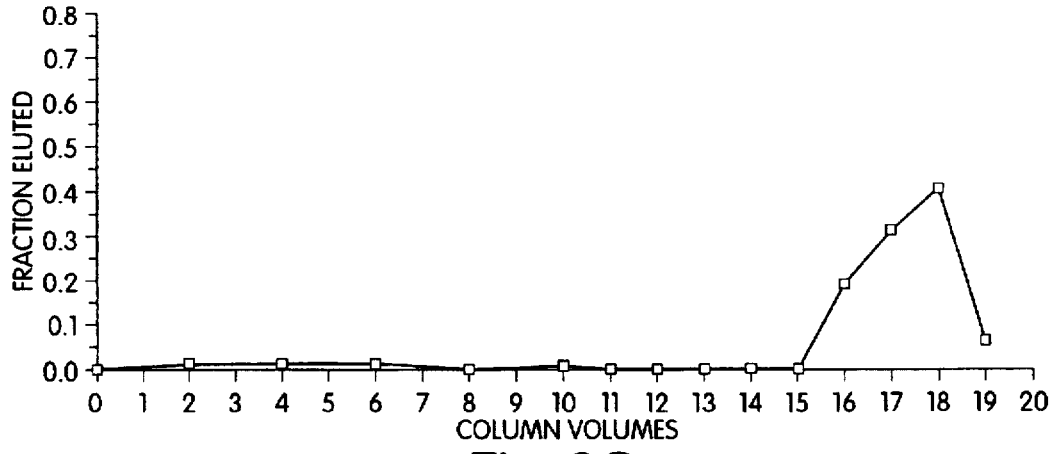
Figure 10:
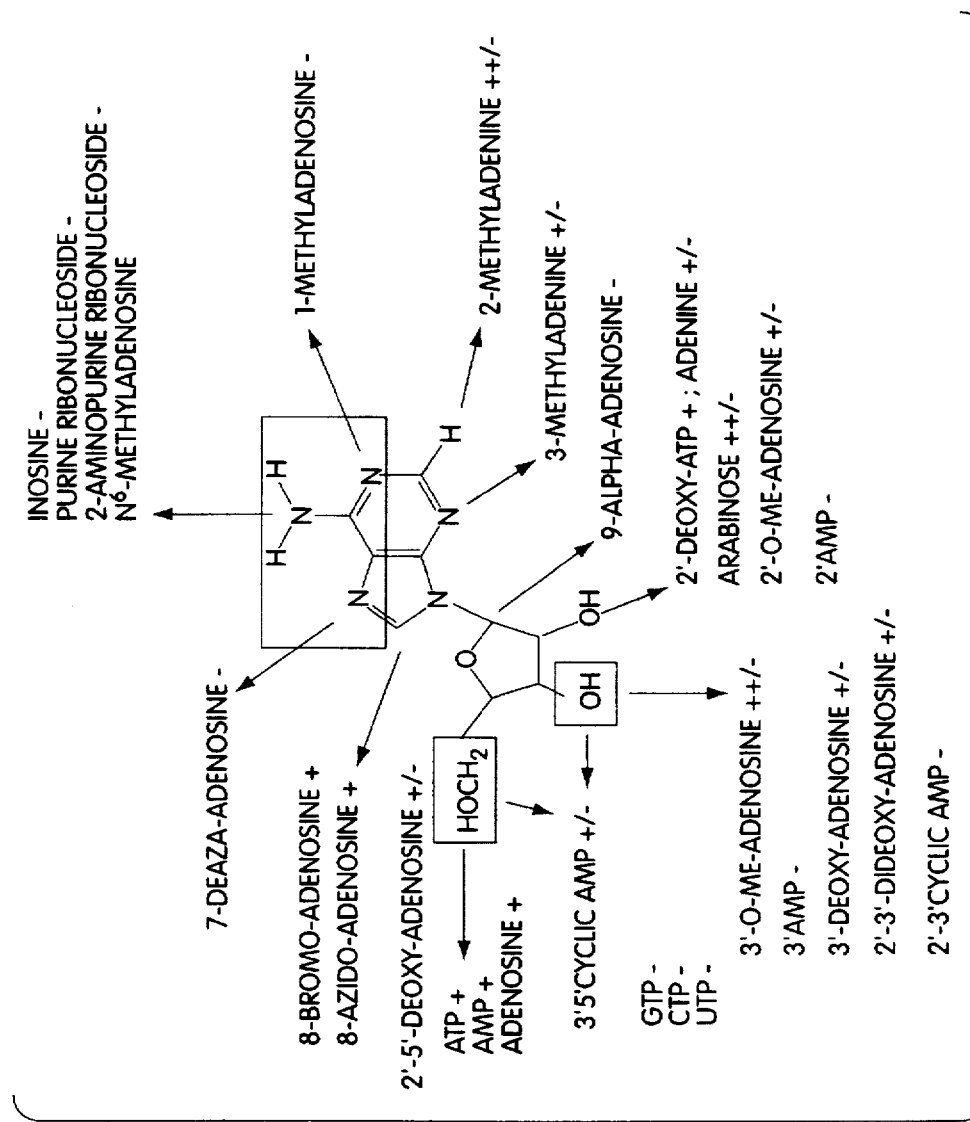
FIG. 10 is a schematic diagram showing the specifity of the adenosine/ATP aptamer, as determined by analog elution experiments. ++, 85–100% of DNA eluted in 3 column volumes of 1.5 mM ligand; +, 70–84% of DNA eluted in 3 column volumes of 1.5 mM ligand; +/−, 6%–69% of DNA eluted in 3 column volumes of 1.5 mM ligand; −, <5% of DNA eluted in 3 column volumes of 1.5 mM ligand. The regions most important for binding are highlighted by the shaded boxes.

The first and second GG pairs, and the third and fourth GG pairs, are connected by single purine residues. These single base 'loops', referred to as L1 and L3, lie below the bottom quartet, and by analogy with the thrombin aptamer structure, would span the minor groove sides of this quartet. Molecular modeling indicates that a single nucleotide could potentially span the width of the minor grooves (P. Schultze and J. Feigon, pers. comm.). In the secondary selection from the mutagenized pool, L1 was predominantly a G, and L3 was always a purine. The corresponding loops in the thrombin aptamer are TT doublets. It was therefore of interest to see if changing L1 and L3 to TT would be consistent with ATP binding activity. The corresponding oligonucleotide was synthesized (FIGS. 5D, 8D SEQ ID NOS:93–102,129), but did not show detectable binding to the ATP-agarose column, suggesting that the single-base loops may cause a distortion of the G-quartets that is essential to binding.

In contrast to the length and/or sequence specificity of L1 and L3,neither the sequence nor the length of L2, the loop that closes the P2 stem are critical. This region is highly variable in the secondary selection.

Conserved Adenosine Residues

The invariant nature of A9 and A22 in the selection from the mutagenized pool indicated that these residues were critical for aptamer structure, ligand interaction, or both. Substitution of 2'-deoxycytidine, 2'-deoxyguanosine, or thymidine for A9, or deletion of A9, results in complete loss of binding (FIG. 5E SEQ ID NOS:103–108; FIG. 6). Substitution of 7-deaza-2'deoxyadenosine (FIG. 6) at this position also eliminates binding to the ATP-agarose column, and substitution 2'-deoxynebualrine (purine riboside) (FIG. 6) at this position reduces binding.

The corresponding substitutions at A22 gave a more complex pattern. Binding to the ATP-agarose column was eliminated by 2'-deoxycytidine, a 2'-deoxyguanosine, or a thymidine substitution. Remarkably, deletion of A22 reduced but did not eliminate binding; in addition 7-deaza-2'deoxyadenosine substitution did not eliminate binding and the 2'-deoxynebularine substitution had no effect (FIG. 5F SEQ ID NOS:109–118; FIG. 6). A closer inspection of the primary sequence provided a possible explanation for this inconsistency, in that A22 is followed immediately by another A residue in the DH25.42 sequence. Although A23 is normally paired with T3 in the P1 stem, it seemed possible that in the absence of A22, A23 could replace A22, with P1 being reconstituted as a two base-pair stem (C2:G25, T3:G24). To test this hypothesis, a new set of oligonucleotides were synthesized (FIG. 5F) which changed the T3:A23 base-pair to C3:G23. In this context, substitution of 2'-deoxycytidine, 2'-deoxyguanosine, or thymidine for A22, as well as deletion of A22, eliminated binding. Furthermore, in this context, 7-deaza-2'deoxyadenosine at position 22 eliminated binding, and 2'-deoxynebularine substitution reduced binding. These results support the involvement of N7 and N6 of both A9 and A22, either directly or indirectly, in ligand binding.

Isolation of Catalytic DNAs

Figure 11:
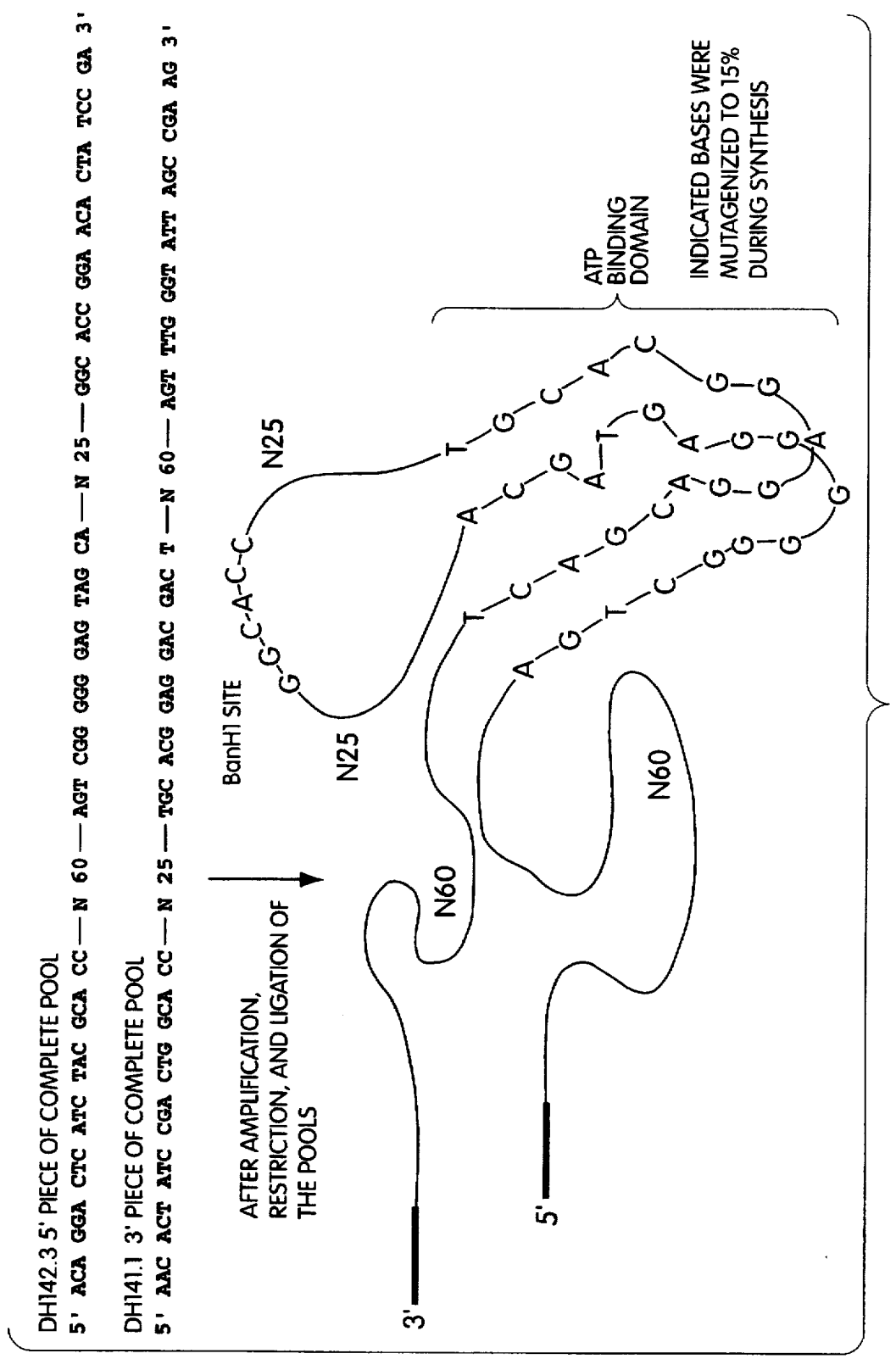
FIG. 11 is a schematic representation of candidate catalytic DNAs (SEQ ID NOS:129–132) of the invention.

Single-stranded, catalytic DNA molecules may be isolated that function in conjunction with ATP or ATP-γ-S to transfer one or more of the adenyl phosphates to either the 5' or 3' OH of a DNA substrate. These molecules are isolated from a random sequence pool of DNAs that contain an ATP binding domain (as described herein and shown in FIG. 11 SEQ ID NOS:129–132). The sequence of the ATP binding domain is mutagenized to approximately 15% and is flanked on the 3' and 5' sides by random sequence. There is also random sequence inserted into an apparently nonfunctional part of the ATP binding domain. Two randomly mutagenized oligonucleotides have been synthesized using standard techniques of β-cyanoethyl phosphoramidite chemistry. One consisted of the 5' portion of the final pool, and the other consisted of the 3' portion of the final pool.

Figure 12:
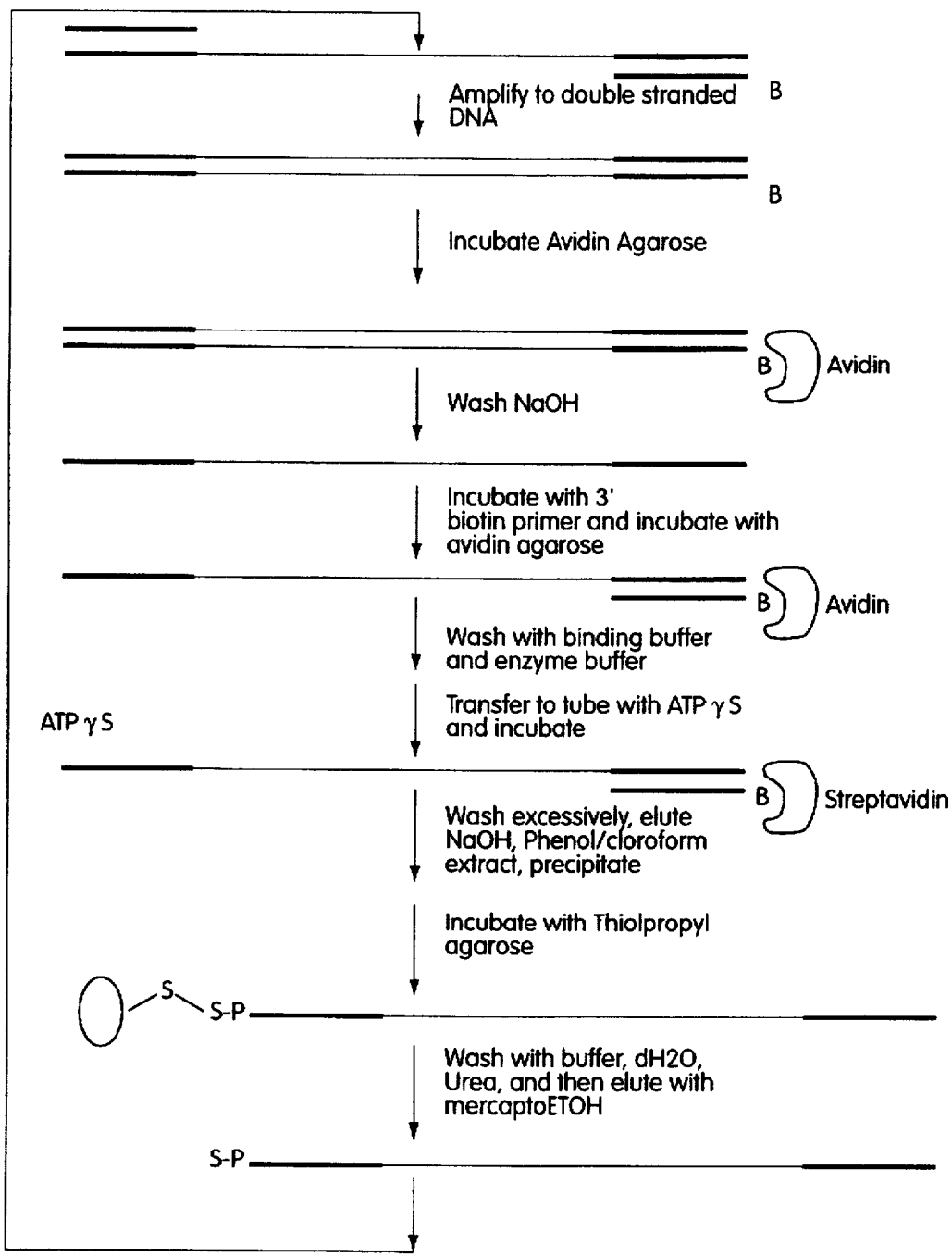
FIG. 12 is a schematic representation of a selection scheme for isolating catalytic DNAs of the invention.

The isolation of molecules from this pool having polynucleotide kinase activity is achieved as follows (FIG. 12). The selection is conducted using a solid support such as avidin-agarose. This approach allows unreacted substrate to be removed by washing the reaction mix away from the bound DNA pool. The reaction is carried out in a 400 mM KCl, 50 mM $MgCl_2$, 5 mM $MnCl_2$, and 25 mM HEPES pH 7.4 buffer. Binding (biotin-avidin-agarose) and washing are carried out in a 1M NaCl, 5 mM EDTA, 25 mM HEPES pH 7.4 buffer.

The selection begins by mixing the pool DNA and the 3' biotinylated primer together (with a 2-fold excess of primer) in binding buffer. $^{32}p$ is also included in this mix to allow monitoring of binding efficiency. The mixture is heated to 80° C. for 5 minutes and then cooled to room temperature. The avidin-agarose (stated binding capacity of 33 nMoles/ml) is used at 11 nMoles/ml, and an appropriate amount of avidin-agarose is utilized for the amount of 3' biotinylated primer added to the mix. The avidin-agarose is preequilibrated with 20 column volumes of binding buffer, and the above mix is added to the avidin-agarose matrix and incubated with rotation for 30 minutes. The avidin-agarose mix is then washed with 5 column volumes of binding buffer and next washed with 5 column volumes of enzyme buffer. Both the avidin-agarose mix and the wash are analyzed by Cerenkov counting. The counts on the matrix divided by the total counts reflects the efficiency of binding of the pool DNA to the avidin-agarose.

The avidin-agarose mixture is next transferred to an appropriate number of 3.5 ml Sarstedt reaction tubes with a small amount of preloaded enzyme buffer and ATP-γ-S is added to a final concentration of 10 mM. The mix is resuspended and placed at 30° C. with rotation for 16–18 hours. Following this incubation, the reactions are cooled to room temperature to ensure maximal annealing of pool DNA to biotinylated oligonucleotide, and the reaction mix is transferred back to small polypropylene columns (Biorad), the columns are washed with 5 column volumes of wash buffer to remove excess substrate, and the DNA eluted by denaturation with 2 column volumes of 10 mM NaOH in 1M Tris pH 7.2. The eluted DNA is then phenol/chloroform extracted, and the supernatant is NaCl/ethanol precipitated.

Those DNAs accelerating the transfer of the thiophosphate of the ATP-γ-S to either the 3' or 5' end of the molecule are identified by this thiophosphate. The thiophosphate is used as a chemical hook to fish out the molecule to which it is attached as follows. The resuspended DNA (in 5 ml of 5 mM HEPES pH 7.4) is loaded onto a 0.5 ml Thiopropyl sepharose column which has been preequilibrated in 5 mM HEPES pH 7.4. This mix is incubated at room temperature for 30 minutes, and those molecules which have a thiophosphate attached react with the Thiopropyl to yield a disulfide bond. The column is then washed with 20 column volumes of wash buffer and 5 column volumes of $dH_2O$. To remove non-specifically bound molecules, the column is washed with 20 column volumes of 3M Urea, 5 mM EDTA, and, to remove the severely denaturing buffer, the column is washed with 10 column volumes of water. Specifically bound molecules are collected upon reduction of the disulfide bond in 150 mM mercaptoethanol in 0.5× wash buffer.

The collected eluate, wash fractions, and matrix are then Cerenkov counted to determine the extent of reaction and collection. The mercaptoethanol fraction is then NaCl/ethanol precipitated in the presence of glycogen.

Precipitated molecules are amplified by standard PCR techniques in the presence of [α-$^{32}$P]dATP to label the amplified strands. The reaction mixture is then phenol/chloroform extracted and NaCl/ethanol precipitated. The precipitate is resuspended in 0.3 ml of 100 mM Tris pH 7.6, 100 mM NaCl (AB buffer), and loaded onto an appropriate amount of avidin-agarose (11 nMoles/ml binding capacity) column preequilibrated with 20 column volumes of AB buffer. The column is washed with 20 column volumes of 1× AB buffer, and the desired single-stranded DNA molecule collected by denaturation (using 2 column volumes of 100 mM NaOH in water) of the double-stranded DNA annealed to the avidin-agarose column through the biotinylated 3' PCR primer. The eluted single-stranded DNA is then NaCl/ethanol precipitated and resuspended in binding buffer.

By repeating the above procedure a number of times, a pool of single stranded DNA molecules enriched for the ability to transfer a thiophosphate from ATP-γ-S to the 3' or 5' OH is obtained. By determining the substrate specificity required for the self modification, exogenous substrates are designed so that these isolated molecules act in trans to label inputted oligonucleotides with a thiophosphate.

Methods in the art may be used at particular steps of this isolation procedure and one skilled in the art is referred to Ellington and Szostak, Nature 346: 818–822 (1990); Lorsch and Szostak, Nature 371: 31–36 (1994); Tuerk and Gold, Science 249: 505–510 (1990); and methods described herein.

The following materials and methods were used by applicants to obtain the results described herein.

DNA Pools

The pool of random-sequence DNA molecules that was used in this work has been previously described (Bartel et al., Science 261:1411, (1993)); the particular pool we used contained ≅2 * $10^{14}$ different molecules with 72 random nucleotides flanked by defined primer binding sites.

The mutagenized pool used in the secondary selection was based on the sequence 5'-GTGCTT GGGGGAGTAT- TGCGGAGGAAAGCGGCCCTGCTGAA G-3'(SEQ ID NO:133), flanked by the same primer binding sites as in the original random-sequence pool. During the synthesis the central domain was mutagenized to an extent of ≅30%, i.e. each nucleotide had a 10% chance of mutating to each other base (Bartel et al., Science 261:1411, (1993); Green et al., Methods: A Companion to Methods in Enzymology 2:75–86, (1991)). 480 μg of DNA was recovered after deprotection and purification by polyacrylamide gel electrophoresis; a primer extension reaction using a limiting amount of the 3' primer indicated that 19% of the DNA could be copied into a complementary strand, implying a yield of 92 μg or 2 * $10^{15}$ molecules of amplifiable DNA.

Polymerase Chain Reaction (PCR)

PCR reactions contained 200 μM of each dNTP, 10 mM Tris-HCl pH 8.4, 50 mM KCl, 2.5 mM $MgCl_2$, and 2.5 Units of Taq polymerase per 100 μl reaction. Primer concentrations were 1 μM crude oligonucleotide or 0.5 μM if gel purified. 5' primers were: DH22.23, 5'GGAACACTATCCGACTGGCACC-3'(SEQ ID NO:134) and D33.70; the 3' primer was D20.99; the latter two primers are described in Bartel et al., Science 261:1411, (1993). Thermal cycling was 94° C. for 45 seconds, 52°–54° C. for 70 seconds and 72° C. for 45 seconds.

Single stranded DNA was generated by removing 1/10 of a PCR reaction for use as a template in a second PCR reaction with no added 3' primer. 1 μM of the oligonucleotide DH20.117 5'-CCTTGGTCATTAGGATCC-3'(SEQ ID NO:135), the complement of the 3' primer, was added to inactivate the remaining 3' primer and maximize the fraction of DNA synthesis resulting from extension of the 5' primer. Radioactively labeled DNA was synthesized by including [α-$^{32}$P]dATP in the primer extension reaction. 15 cycles of primer extension were used for single stranded DNA synthesis.

Amplification of the synthetic DNA pool requires a large PCR volume (10–500 ml) to ensure efficient amplification of all molecules, so that pool complexity is maintained. Thermal cycling of large volumes was done manually in water baths. The DNA was initially melted at 96° C. for 8 minutes. Cycles of PCR were 94° C. for 4 minutes, 42° C. for 5–6 minutes, and 72° C. for 7 minutes. The final extension was for 20 minutes. For the first round of the original selection, a 21 ml single strand synthesis reaction was done for 6 cycles with 60 μg of double stranded DNA as template. Single-stranded DNA from the mutagenized pool was generated in a 48 ml reaction with 9.2 μg of synthetic DNA as template. This template was amplified for two cycles with both 5' and 3' primers, after which the 3'-complement DH20.117 was added to 1 μM, followed by 8 cycles of primer extension. After PCR the DNA was phenol/chloroform extracted and gel purified (Sambrook et al., Molecular Cloning 2d ed., Cold Spring Harbor Laboratory Press, (1989)).

Selections

ATP agarose (Sigma) columns of 1 ml bed volume (1–3 mM ATP) (FIG. 2A) were pre-equilibrated with approximately 25 ml of column buffer (300 mM NaCl, 5 mM MgCl $_2$, 20 mM Tris pH 7.6). Single stranded DNA, (150 μg in the first round of selection and thereafter 1–5 μg, 0.03–0.13 nmol, labeled with [α-$^{32}$P]dATP as described above) in the same buffer was heated to 75° C. for 5 minutes, cooled to room temperature for 20–30 minutes, and loaded onto the column. After equilibrating for ≅5 minutes, the column was washed with 5 ml of column buffer (10 ml during selection from the mutagenized pool). The remaining DNA was specifically eluted with 3 ml of column buffer containing 3 mM ATP. Each 1 ml fraction was then analyzed by Cerenkov counting. The first two fractions (3 in the secondary selection) after starting ligand elution were collected, ethanol precipitated, and residual ATP was removed by Sephadex spin-column chromatography. This DNA was then used as a template for PCR amplification.

Preparation of Synthetic Oligonucleotides for Binding Assays

DNA was synthesized by solid phase β-cyanoethyl phosphoramidite chemistry on a Milligen/Biosearch Model 8750 or Millipore Expedite automated synthesizer. Nucleoside phosphoramidite analogs (Glen Research) were coupled manually to conserve material. Deprotected synthetic DNA was extracted with n-butanol (Sawadago et al., *Nucleic Acids Res.* 19:674, (1991)) and purified by polyacrylamide gel electrophoresis. 50–75 μg (6–9 nmol) of DNA was 5' phosphorylated with $^{32}$P using T4 polynucleotide kinase (New England Biolabs) and then affinity purified on an ATP-agarose affinity column. This purification step was necessary because of variation in the quality and purity of synthetic DNA. The ATP eluted DNA was ethanol precipitated, resuspended in $H_2O$, and residual ATP was removed by Sephadex spin column chromatography.

The complex of oligonucleotides DH20.155 and DH21.82 was assembled by heating 14 μM $^{32}$P-labeled DH20.155 and 270 μM DH21.82 to 75° C. for 5 minutes followed by cooling to room temperature.

Binding Assays

10–500 ng (1.2 pmol–60 pmol) of affinity purified DNA was loaded onto a ¼ ml bed volume ATP-agarose column pre-equilibrated with column buffer. After 2–5 min., the column was washed with 10 column volumes of buffer. The remaining bound DNA was eluted with 3 column volumes of 3 mM ATP in the same buffer. Each fraction was then analyzed by Cerenkov counting. The number of counts in the specifically eluted fractions was then divided by the total loaded onto the column to give the fraction eluted.

Determination of the Equilibrium Dissociation Constants

The $K_d$ for adenosine was measured by analytical ultrafiltration (Jenison et al., *Science* 263:1425–1429, (1994)). In this technique bound and unbound ligand partition across a membrane in a ultra filtration device. DNA (0.06 μM–30 μM) was incubated for 5 min. at room temperature in 200 μl of column buffer containing 5.49 nM [2,8,5'$^3$H] adenosine. The reaction mixture was loaded onto an Microcon 10 microconcentrator (Amicon) and spun at 14000 RPM in an Eppendorf 5415 centrifuge for 4 min., resulting in 100 μl of ultrafiltrate. This method could not be used with ATP because only 30% of ATP passed through the filter in 50% of the volume. Even with adenosine, only 40–45% passed through in 50% of the volume. The $K_d$ was estimated from the concentration of DNA calculated to decrease the amount of adenosine passing through the filter by 50%. During the course of the experiment the DNA concentration increases by a factor of two since the DNA is retained above the filter; therefore, using the initial DNA concentration would give an artificially low $K_d$, and using the final DNA concentration would give an artificially high $K_d$. The $K_d$ reported is the average of these two estimates. At 12 μM DNA the fraction of adenosine retained was independent of adenosine concentration over a range from 1.65 nM to 165 nM.

Cloning and Sequencing

PCR amplified DNA from the round 8 pool of the primary selection was cloned by restriction enzyme cleavage at the EcoRI (added by PCR with primer DH31.41 5'GCGGAAT-TCGGAACACTATCCGACTGGCACC 3' SEQ ID NO:136) and BamHI sites in the primer regions, followed by ligation with an EcoRI-BamHI digested vector. PCR amplified DNA from round 4 of the secondary selection was cloned by the T/A cloning method using a kit manufactured by Invitrogen. Sequencing was by the dideoxy method using Sequenase from United States Biochemical Co. using their protocols.

USE

DNA aptamers that bind adenosine or an adenosine-5'-phosphate find use as purification reagents for isolating those molecules. For example, a DNA aptamer that binds ATP may be immobilized on a column or other solid support, and ATP may be purified from a sample by contact with that column or support. Alternatively, an aptamer of the invention can be used to determine the amount or sub-cellular localization of, for example, ATP in vivo. Introduction of the aptamer into a cell is preferably accomplished by microinjection, and ATP is quantitated or qualitatively detected by detection of a label bound to the aptamer.

Catalytic DNAs produced by the method of the invention can be used as in vitro or in vivo catalysts. In some cases the nucleic acids may be used to detect the presence of the ligand. For example, the nucleic acid may bind the ligand and catalyze a reaction which converts the ligand into a readily detectable molecule. The catalytic DNAs created by the method of the invention can also be used in assays to detect molecules modified by the DNAs which are not themselves ligands, e.g., a DNA phosphorylated by a polynucleotide kinase catalyst.

Other embodiments are within the following claims.

---

What is claimed is:

1. A method for producing a single-stranded DNA molecule that binds adenosine or an adenosine-5'-phosphate, comprising the steps of:

a) providing a population of DNA molecules each having a region of random sequence;

b) contacting said population with adenosine or adenosine-5'-phosphate;

c) isolating a subpopulation of said population by partitioning DNA molecules in said population which specifically bind said adenosine or adenosine-5'-phosphate from those which do not;

d) amplifying said subpopulation in vitro;

e) optionally repeating steps b–d for said amplified subpopulation;

f) obtaining from said amplified subpopulation a single-stranded DNA molecule capable of binding adenosine or an adenosine-5'-phosphate.

2. The method of claim 1, wherein said adenosine-5'-phosphate is ATP.

3. A single-stranded DNA molecule which binds adenosine or an adenosine-5'-phosphate.

4. The DNA molecule of claim 3, wherein said DNA comprises a guanosine-rich region.

5. The DNA molecule of claim 4, wherein said guanosine-rich region forms a G-quartet.

6. The DNA molecule of claim 4, wherein said DNA comprises adenosine residues adjacent said guanosine-rich region.

7. The DNA molecule of claim 4, wherein said DNA molecule comprises one or more base-paired nucleic acids adjacent said guanosine-rich region.

8. The DNA molecule of claim 7, wherein said base-paired nucleic acids form stem or stem-loop structures.

9. A method for producing a catalytic DNA molecule capable of binding a first ligand and catalyzing a chemical reaction modifying said DNA molecule, comprising the steps of:

a) providing a first population of DNA molecules each having a first region of random sequence;

b) contacting said first population of DNA molecules with said first ligand;

c) isolating a first ligand-binding subpopulation of said first population of DNA molecules by partitioning DNA molecules in said first population which specifically bind said first ligand from those which do not;

d) amplifying said first ligand-binding subpopulation in vitro;

e) identifying a first ligand binding sequence;

f) preparing a second population of DNA molecules each of said DNA molecules comprising said first ligand binding sequence and a second region of random sequence;

g) contacting said second population of DNA molecules with a second ligand capable of binding said first ligand binding sequence; and h) isolating a subpopulation of said catalytic DNA molecules from said second population of DNA molecules by partitioning DNA molecules which have been modified in step g) from those which have not been modified.

10. The method of claim 9 wherein said first ligand is ATP.

11. The method of claim 9 wherein said second ligand serves as a substrate for said chemical reaction.

12. The method of claim 9 wherein said catalytic DNA molecule transfers a phosphate from a nucleotide triphosphate to said catalytic DNA molecule.

* * * * *

UNITED STATES PATENT AND TRADEMARK OFFICE
CERTIFICATE OF CORRECTION

PATENT NO. : 5,631,146
DATED : May 20, 1997
INVENTORS : Jack W. Szostak et al.

It is certified that error appears in the above-identified patent and that said Letters Patent is hereby corrected as shown below:

Column 5, line 18, replace "of proximal-most" with --of the proximal-most--;

Column 10, line 30, replace "(SEQ ID NOS:)" with --(SEQ ID NOS: 1-45)--;

Column 10, line 32, replace "(SEQ ID NO:1-45))" with --(SEQ ID NOS: 1-45))--;

Column 10, line 57, replace "SEQ ID NOS: 47-60" with --; SEQ ID NO: 46--;

Column 12, line 49, replace "SEQ ID NOS: 125-127" with --SEQ ID NOS: 126-127--;

Column 14, line 19, replace "SEQ ID NOS: 129-132" with --SEQ ID NOS: 130-132--.

Signed and Sealed this

Sixteenth Day of September, 1997

Attest:

BRUCE LEHMAN

*Attesting Officer*      Commissioner of Patents and Trademarks

SEQUENCE LISTING ( 1 ) GENERAL INFORMATION:

( i i i ) NUMBER OF SEQUENCES: 136

( 2 ) INFORMATION FOR SEQ ID NO:1:

( i ) SEQUENCE CHARACTERISTICS:
        ( A ) LENGTH: 41 base pairs
        ( B ) TYPE: nucleic acid ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

GTGCTTGGGG GAGTATTGCG GAGGAAAGCG GCCTGCTGAA G         41

( 2 ) INFORMATION FOR SEQ ID NO:2:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

GTGCTTGGGG GAATATTGTG GAGGAAAGCG GCCTGCCACC AG        42

( 2 ) INFORMATION FOR SEQ ID NO:3:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

ATGCTTGGGG GAGGAATGCG GAGGAAATTA GTCTGGTGCG G         41

( 2 ) INFORMATION FOR SEQ ID NO:4:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

TCGATTGGGG GAGTATTGCG GTGGAAATCG AGGTTGATTA AT        42

( 2 ) INFORMATION FOR SEQ ID NO:5:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

ATGCTTGGGG GAGGCTTTCG GAGGAAAGCG TCGGTCGTGT CG        42

( 2 ) INFORMATION FOR SEQ ID NO:6:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

TTGCTTGGGG GAGTATTTCG GAGGAAAGCA GTGCTGCTAA AG                 4 2

( 2 ) INFORMATION FOR SEQ ID NO:7:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

TTGCTTGGGG GAGCGTACGA GGAAAGCCTC CCTGTCTGAC TG                 4 2

( 2 ) INFORMATION FOR SEQ ID NO:8:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

GTGCTTGGGG GAGTAGAATG GAGGAAAGCG CGATTGTTGC AA                 4 2

( 2 ) INFORMATION FOR SEQ ID NO:9:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

GCGTTTGGGG GAGGAGAACG GAGGAAAACG GCCGCCCTGA GT                 4 2

( 2 ) INFORMATION FOR SEQ ID NO:10:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

GTGCTTGGGG GAGTACTGCG GGGAGAGCG ACCGTGCTGG TC                  4 2

( 2 ) INFORMATION FOR SEQ ID NO:11:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

TTGCCTGGGG GAACATTGTG GAGGAAGCAG GGTGTAGTGG GC                 4 2

( 2 ) INFORMATION FOR SEQ ID NO:12:

( i ) SEQUENCE CHARACTERISTICS:
    ( A ) LENGTH: 42 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:12:

AAGCATGGGG GAGTCTTGCG GAGGAATGCG CACCACGTGT CG            42

( 2 ) INFORMATION FOR SEQ ID NO:13:

( i ) SEQUENCE CHARACTERISTICS:
    ( A ) LENGTH: 43 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:13:

TGGTTTTCGG GGGAGTCTGA GGAGGAAAAC GCCACGGCTA ACG           43

( 2 ) INFORMATION FOR SEQ ID NO:14:

( i ) SEQUENCE CHARACTERISTICS:
    ( A ) LENGTH: 42 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:14:

CTGATTGGAG GAGTATTGCG GGGGAAATCG GGCCTGCTAA AG            42

( 2 ) INFORMATION FOR SEQ ID NO:15:

( i ) SEQUENCE CHARACTERISTICS:
    ( A ) LENGTH: 41 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:15:

ATGATTGGAG GAGCATCGCG GGGAAAGGGG CTCTGCTAAA G             41

( 2 ) INFORMATION FOR SEQ ID NO:16:

( i ) SEQUENCE CHARACTERISTICS:
    ( A ) LENGTH: 41 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:16:

GTGATTGGGG GAGCATTGCG AGGAAAAATG CGCGTGTGAT G             41

( 2 ) INFORMATION FOR SEQ ID NO:17:

( i ) SEQUENCE CHARACTERISTICS:
    ( A ) LENGTH: 42 base pairs
    ( B ) TYPE: nucleic acid

```
          ( C ) STRANDEDNESS: single
          ( D ) TOPOLOGY: linear ( i i ) MOLECULE TYPE: DNA (genomic)

( x i ) SEQUENCE DESCRIPTION: SEQ ID NO:17:

CTACCTGGGG GAGCATTGGG GAGGAAGGTA GCCGTGCGAA AA                              42

( 2 ) INFORMATION FOR SEQ ID NO:18:

( i ) SEQUENCE CHARACTERISTICS:
          ( A ) LENGTH: 41 base pairs
          ( B ) TYPE: nucleic acid
          ( C ) STRANDEDNESS: single
          ( D ) TOPOLOGY: linear ( i i ) MOLECULE TYPE: DNA (genomic)

( x i ) SEQUENCE DESCRIPTION: SEQ ID NO:18:

AAGTTGGGGG AGTATTGCGG AGGAAAGCTG CACTACAGGT G                               41

( 2 ) INFORMATION FOR SEQ ID NO:19:

( i ) SEQUENCE CHARACTERISTICS:
          ( A ) LENGTH: 42 base pairs
          ( B ) TYPE: nucleic acid
          ( C ) STRANDEDNESS: single
          ( D ) TOPOLOGY: linear ( i i ) MOLECULE TYPE: DNA (genomic)

( x i ) SEQUENCE DESCRIPTION: SEQ ID NO:19:

AAGCTCGGGG GAGTATCGCG GAGGAGAGCG GCTAAGATTA TG                              42

( 2 ) INFORMATION FOR SEQ ID NO:20:

( i ) SEQUENCE CHARACTERISTICS:
          ( A ) LENGTH: 42 base pairs
          ( B ) TYPE: nucleic acid
          ( C ) STRANDEDNESS: single
          ( D ) TOPOLOGY: linear ( i i ) MOLECULE TYPE: DNA (genomic)

( x i ) SEQUENCE DESCRIPTION: SEQ ID NO:20:

CTGCTTGGAG GAGAATCGCG GGGGAAAGAG GATGTGCTCA AA                              42

( 2 ) INFORMATION FOR SEQ ID NO:21:

( i ) SEQUENCE CHARACTERISTICS:
          ( A ) LENGTH: 40 base pairs
          ( B ) TYPE: nucleic acid
          ( C ) STRANDEDNESS: single
          ( D ) TOPOLOGY: linear ( i i ) MOLECULE TYPE: DNA (genomic)

( x i ) SEQUENCE DESCRIPTION: SEQ ID NO:21:

GACTTGGGGG AGCATTGCGA GGAAAACGGC GCAGAACAAC                                 40

( 2 ) INFORMATION FOR SEQ ID NO:22:

( i ) SEQUENCE CHARACTERISTICS:
          ( A ) LENGTH: 42 base pairs
          ( B ) TYPE: nucleic acid
          ( C ) STRANDEDNESS: single
          ( D ) TOPOLOGY: linear ( i i ) MOLECULE TYPE: DNA (genomic)
```

( x i ) SEQUENCE DESCRIPTION: SEQ ID NO:22:

CTACCTGGGG GAGCATTGGG GAGGAAGGTA GCCGTGCGAA AA  42

( 2 ) INFORMATION FOR SEQ ID NO:23:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:23:

GTGCGTGGGG GAAAATTTTG GAGGAATGCG ACGCTGCTGA A  41

( 2 ) INFORMATION FOR SEQ ID NO:24:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:24:

GTGATTGGGG GAGCATAGCG GAGGAAATCA ACCCTACTGA AC  42

( 2 ) INFORMATION FOR SEQ ID NO:25:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:25:

GTCCTTGGGG GAGCGTACAG GGAAAACGCG GTAATCATGA TG  42

( 2 ) INFORMATION FOR SEQ ID NO:26:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:26:

GTTCTTGGGG GAGTAGTACG GAGGAAAGCA GTCGTGATAT GG  42

( 2 ) INFORMATION FOR SEQ ID NO:27:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:27:

GTGATTGGGG GAATATTGTG GAGGAAAGAA GCCGTGCCGA CC  42

( 2 ) INFORMATION FOR SEQ ID NO:28:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:28:

```
TATCTTGGGG GAACATGCTG GCGGAAAGCT AGAGTGCTCA AA                    42
```

( 2 ) INFORMATION FOR SEQ ID NO:29:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:29:

```
ATGCGTGGGG GAGCATTACG GAGGAACGCT TGCTTGCTGA AC                    42
```

( 2 ) INFORMATION FOR SEQ ID NO:30:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:30:

```
GAGCTCGGGG GAGTATTATG GAGGAGAGCG ACCTTGCTGA CG                    42
```

( 2 ) INFORMATION FOR SEQ ID NO:31:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:31:

```
ACACTTGGAG GAGTATGGCG GGGAGAGTA GCAGTTCCGA AT                     42
```

( 2 ) INFORMATION FOR SEQ ID NO:32:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:32:

```
TCGATTGGGG GAATAACGTG GAGGAAATCG CCTATTCTGA AG                    42
```

( 2 ) INFORMATION FOR SEQ ID NO:33:

( i ) SEQUENCE CHARACTERISTICS:
        ( A ) LENGTH: 42 base pairs
        ( B ) TYPE: nucleic acid (C) STRANDEDNESS: single
(D) TOPOLOGY: linear (ii) MOLECULE TYPE: DNA (genomic)

(xi) SEQUENCE DESCRIPTION: SEQ ID NO:33:

CACTTTGGGG GAGTCTTGCG GAGGAGAACG TGCGTGCAGA CC 42

(2) INFORMATION FOR SEQ ID NO:34:

(i) SEQUENCE CHARACTERISTICS:
(A) LENGTH: 42 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:34:

TTGCGTGGGG GAACATTGTG GAGGAACGCG GCCGTACAGA TG 42

(2) INFORMATION FOR SEQ ID NO:35:

(i) SEQUENCE CHARACTERISTICS:
(A) LENGTH: 42 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:35:

GTTTTGGGGG AGAATTCGG AGGAAAGCAA GGTCGTGCTT AG 42

(2) INFORMATION FOR SEQ ID NO:36:

(i) SEQUENCE CHARACTERISTICS:
(A) LENGTH: 42 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:36:

GCGCTTGGGG GAAAATTGTG GAGGAAAGCA CCCCAGTTGT TA 42

(2) INFORMATION FOR SEQ ID NO:37:

(i) SEQUENCE CHARACTERISTICS:
(A) LENGTH: 41 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:37:

GAGCTTGGGG GAGCATTGCG AGGGAAGCTG GGGTGTTTAT G 41

(2) INFORMATION FOR SEQ ID NO:38:

(i) SEQUENCE CHARACTERISTICS:
(A) LENGTH: 42 base pairs
(B) TYPE: nucleic acid
(C) STRANDEDNESS: single
(D) TOPOLOGY: linear (ii) MOLECULE TYPE: DNA (genomic)

( x i ) SEQUENCE DESCRIPTION: SEQ ID NO:38:

GGCAGTGGGG GAGGAATGCG GAGGAATGTA GCCCGGTGGA AG    42

( 2 ) INFORMATION FOR SEQ ID NO:39:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:39:

GTGCTTGGGG GAGTATTGTG GAGGAAAGCA CACCTGTTCA CG    42

( 2 ) INFORMATION FOR SEQ ID NO:40:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:40:

GTGGTTGGGG GAGCAATGCG AGGAAATCCG GTGCGCTGAA TC    42

( 2 ) INFORMATION FOR SEQ ID NO:41:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:41:

GATCGGGGGA GAGAATAGCG GAGGAGATCG TCCCTGCTGA GG    42

( 2 ) INFORMATION FOR SEQ ID NO:42:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:42:

GTGCTCGGGG GAACCTTGTG GAGGAGAAGC GCATTACGGT GTTT    44

( 2 ) INFORMATION FOR SEQ ID NO:43:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:43:

GTGCATGGGG GAAGTATGAC GGGGGAATGC AGCCCGGATG AAG    43

( 2 ) INFORMATION FOR SEQ ID NO:44:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:44:

CTTTTTGGGG GAGTATTTAC GGAGGAAAAT TGCAGTGACT GAAC        44

( 2 ) INFORMATION FOR SEQ ID NO:45:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:45:

CTTGTTGGGG GAGTACTACG GGAGGAAACA GGGTTCCTGA AG        42

( 2 ) INFORMATION FOR SEQ ID NO:46:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:46:

CCTGGGGGAG TATTGCGGAG GAAGG        25

( 2 ) INFORMATION FOR SEQ ID NO:47:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:47:

TGGGGAGTA TTGCGGAGGA A        21

( 2 ) INFORMATION FOR SEQ ID NO:48:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:48:

CTGGGGGAGT ATTGCGGAGG AAG        23

( 2 ) INFORMATION FOR SEQ ID NO:49:

( i ) SEQUENCE CHARACTERISTICS:
        ( A ) LENGTH: 25 base pairs
        ( B ) TYPE: nucleic acid (C) STRANDEDNESS: single
        (D) TOPOLOGY: linear (ii) MOLECULE TYPE: DNA (genomic)

(xi) SEQUENCE DESCRIPTION: SEQ ID NO:49:

CCTGGGGGAG TATTGCGGAG GAAGG    25

(2) INFORMATION FOR SEQ ID NO:50:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:50:

TCCTGGGGGA GTATTGCGGA GGAAGGA    27

(2) INFORMATION FOR SEQ ID NO:51:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:51:

CCTGGGGGAC ATTGGGAGGA AGG    23

(2) INFORMATION FOR SEQ ID NO:52:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:52:

CCTGGGGGAG ATTCGGAGGA AGG    23

(2) INFORMATION FOR SEQ ID NO:53:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:53:

CCTGGGGGAC ATTGGGGAGG AAGG    24

(2) INFORMATION FOR SEQ ID NO:54:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

( x i ) SEQUENCE DESCRIPTION: SEQ ID NO:54:

CCTGGGGAG CATTGGGGAG GAAGG 25

( 2 ) INFORMATION FOR SEQ ID NO:55:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:55:

CCTGGGGAG CATTGCGGAG GAAGG 25

( 2 ) INFORMATION FOR SEQ ID NO:56:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:56:

CCTGGGGAG TATTGCGGAG GAAGG 25

( 2 ) INFORMATION FOR SEQ ID NO:57:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:57:

CCTGGGGAG CTATTAGCGG AGGAAGG 27

( 2 ) INFORMATION FOR SEQ ID NO:58:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:58:

CCTGGGGAG AGATTCTGGA GGAAGG 26

( 2 ) INFORMATION FOR SEQ ID NO:59:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:59:

CCTGGGGAG AGATTACTGG AGGAAGG 27

( 2 ) INFORMATION FOR SEQ ID NO:60:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:60:

CCTGGGGGAG TAGATTCTAG GAGGAAGG                 2 8

( 2 ) INFORMATION FOR SEQ ID NO:61:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:61:

CCTAGGGGAG TATTGCGGAG GAAGG                  2 5

( 2 ) INFORMATION FOR SEQ ID NO:62:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:62:

CCTGGGGGAG TATTGCGGAG GAAGG                  2 5

( 2 ) INFORMATION FOR SEQ ID NO:63:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:63:

CCTGGGGGAG TATTGCGGAG GAAGG                  2 5

( 2 ) INFORMATION FOR SEQ ID NO:64:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:64:

CCTTGGGGAG TATTGCGGAG GAAGG                  2 5

( 2 ) INFORMATION FOR SEQ ID NO:65:

( i ) SEQUENCE CHARACTERISTICS:
    ( A ) LENGTH: 25 base pairs
    ( B ) TYPE: nucleic acid ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:65:

CCTGAGGGAG TATTGCGGAG GAAGG 25

( 2 ) INFORMATION FOR SEQ ID NO:66:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:66:

CCTGGGGAG TATTGCGGAG GAAGG 25

( 2 ) INFORMATION FOR SEQ ID NO:67:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:67:

CCTGGGGGAG TATTGCGGAG GAAGG 25

( 2 ) INFORMATION FOR SEQ ID NO:68:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:68:

CCTGTGGGAG TATTGCGGAG GAAGG 25

( 2 ) INFORMATION FOR SEQ ID NO:69:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:69:

CCTGGGAGAG TATTGCGGAG GAAGG 25

( 2 ) INFORMATION FOR SEQ ID NO:70:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:70:

CCTGGGGGAG TATTGCGGAG GAAGG 25

( 2 ) INFORMATION FOR SEQ ID NO:71:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:71:

CCTGGGGGAG TATTGCGGAG GAAGG 25

( 2 ) INFORMATION FOR SEQ ID NO:72:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:72:

CCTGGGTGAG TATTGCGGAG GAAGG 25

( 2 ) INFORMATION FOR SEQ ID NO:73:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:73:

CCTGGGGAAG TATTGCGGAG GAAGG 25

( 2 ) INFORMATION FOR SEQ ID NO:74:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:74:

CCTGGGGGAG TATTGCGGAG GAAGG 25

( 2 ) INFORMATION FOR SEQ ID NO:75:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:75:

CCTGGGGGAG TATTGCGGAG GAAGG 25

( 2 ) INFORMATION FOR SEQ ID NO:76:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:76:

CCTGGGGTAG TATTGCGGAG GAAGG                             25

( 2 ) INFORMATION FOR SEQ ID NO:77:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:77:

CCTGGGGGAG TATTGCAGAG GAAGG                             25

( 2 ) INFORMATION FOR SEQ ID NO:78:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:78:

CCTGGGGGAG TATTGCGGAG GAAGG                             25

( 2 ) INFORMATION FOR SEQ ID NO:79:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:79:

CCTGGGGGAG TATTGCGGAG GAAGG                             25

( 2 ) INFORMATION FOR SEQ ID NO:80:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:80:

CCTGGGGGAG TATTGCTGAG GAAGG                             25

( 2 ) INFORMATION FOR SEQ ID NO:81:

( i ) SEQUENCE CHARACTERISTICS:
        ( A ) LENGTH: 25 base pairs
        ( B ) TYPE: nucleic acid ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:81:

CCTGGGGGAG TATTGCGAAG GAAGG                                                        25

( 2 ) INFORMATION FOR SEQ ID NO:82:

( i ) SEQUENCE CHARACTERISTICS:
            ( A ) LENGTH: 25 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:82:

CCTGGGGGAG TATTGCGGAG GAAGG                                                        25

( 2 ) INFORMATION FOR SEQ ID NO:83:

( i ) SEQUENCE CHARACTERISTICS:
            ( A ) LENGTH: 25 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:83:

CCTGGGGGAG TATTGCGGAG GAAGG                                                        25

( 2 ) INFORMATION FOR SEQ ID NO:84:

( i ) SEQUENCE CHARACTERISTICS:
            ( A ) LENGTH: 25 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:84:

CCTGGGGGAG TATTGCGTAG GAAGG                                                        25

( 2 ) INFORMATION FOR SEQ ID NO:85:

( i ) SEQUENCE CHARACTERISTICS:
            ( A ) LENGTH: 25 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:85:

CCTGGGGGAG TATTGCGGAA GAAGG                                                        25

( 2 ) INFORMATION FOR SEQ ID NO:86:

( i ) SEQUENCE CHARACTERISTICS:
            ( A ) LENGTH: 25 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:86:

CCTGGGGGAG TATTGCGGAG GAAGG 25

( 2 ) INFORMATION FOR SEQ ID NO:87:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:87:

CCTGGGGGAG TATTGCGGAG GAAGG 25

( 2 ) INFORMATION FOR SEQ ID NO:88:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:88:

CCTGGGGGAG TATTGCGGAT GAAGG 25

( 2 ) INFORMATION FOR SEQ ID NO:89:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:89:

CCTGGGGGAG TATTGCGGAG AAAGG 25

( 2 ) INFORMATION FOR SEQ ID NO:90:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:90:

CCTGGGGGAG TATTGCGGAG GAAGG 25

( 2 ) INFORMATION FOR SEQ ID NO:91:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:91:

CCTGGGGGAG TATTGCGGAG GAAGG 25

( 2 ) INFORMATION FOR SEQ ID NO:92:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:92:

CCTGGGGGAG TATTGCGGAG TAAGG　　　　　　　　　　　　　　　　　　25

( 2 ) INFORMATION FOR SEQ ID NO:93:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:93:

CCTGGAGGAG TATTGCGGAG GAAGG　　　　　　　　　　　　　　　　　　25

( 2 ) INFORMATION FOR SEQ ID NO:94:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:94:

CCTGGAGGAG TATTGCGGGG GAAGG　　　　　　　　　　　　　　　　　　25

( 2 ) INFORMATION FOR SEQ ID NO:95:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:95:

CCTGGGGGAG TATTGCGGTG GAGG　　　　　　　　　　　　　　　　　　24

( 2 ) INFORMATION FOR SEQ ID NO:96:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:96:

CCTGGGGGAG TATTGCGGGG GAAGG　　　　　　　　　　　　　　　　　　25

( 2 ) INFORMATION FOR SEQ ID NO:97:

( i ) SEQUENCE CHARACTERISTICS:
        ( A ) LENGTH: 25 base pairs
        ( B ) TYPE: nucleic acid ( C ) STRANDEDNESS: single
( D ) TOPOLOGY: linear ( i i ) MOLECULE TYPE: DNA (genomic)

( x i ) SEQUENCE DESCRIPTION: SEQ ID NO:97:

CCTGGGGGAG TATTGCGGGG GAAGG 25

( 2 ) INFORMATION FOR SEQ ID NO:98:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:98:

CCTGGGGGAG TATTGCGGAG GAAGG 25

( 2 ) INFORMATION FOR SEQ ID NO:99:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:99:

CCTGGGGGAG TATTGCGGAG GAAGG 25

( 2 ) INFORMATION FOR SEQ ID NO:100:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:100:

CCTGGGGGAG TATTGCGGAG GAAGG 25

( 2 ) INFORMATION FOR SEQ ID NO:101:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:101:

CCTGGGGGAG TATTGCGGAG GAAGG 25

( 2 ) INFORMATION FOR SEQ ID NO:102:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:102:

CCTGGTTGGA GTATTGCGGT TGGAAGG 27

( 2 ) INFORMATION FOR SEQ ID NO:103:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:103:

CCTGGGGGCG TATTGCGGAG GAAGG 25

( 2 ) INFORMATION FOR SEQ ID NO:104:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:104:

CCTGGGGGTG TATTGCGGAG GAAGG 25

( 2 ) INFORMATION FOR SEQ ID NO:105:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:105:

CCTGGGGGGG TATTGCGGAG GAAGG 25

( 2 ) INFORMATION FOR SEQ ID NO:106:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:106:

CCTGGGGGGT ATTGCGGAGG AAGG 24

( 2 ) INFORMATION FOR SEQ ID NO:107:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:107:

CCTGGGGGAG TATTGCGGAG GAAGG 25

( 2 ) INFORMATION FOR SEQ ID NO:108:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:108:

CCTGGGGAG TATTGCGGAG GAAGG                                                      25

( 2 ) INFORMATION FOR SEQ ID NO:109:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:109:

CCTGGGGAG TATTGCGGAG GCAGG                                                      25

( 2 ) INFORMATION FOR SEQ ID NO:110:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:110:

CCTGGGGAG TATTGCGGAG GGAGG                                                      25

( 2 ) INFORMATION FOR SEQ ID NO:111:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:111:

CCTGGGGAG TATTGCGGAG GTAGG                                                      25

( 2 ) INFORMATION FOR SEQ ID NO:112:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:112:

CCTGGGGAG TATTGCGGAG GAGG                                                       24

( 2 ) INFORMATION FOR SEQ ID NO:113:

( i ) SEQUENCE CHARACTERISTICS:
    ( A ) LENGTH: 24 base pairs
    ( B ) TYPE: nucleic acid ( C ) STRANDEDNESS: single
( D ) TOPOLOGY: linear ( i i ) MOLECULE TYPE: DNA (genomic)

( x i ) SEQUENCE DESCRIPTION: SEQ ID NO:113:

CCAGGGGAG TATTGCGGAG GTGG 24

( 2 ) INFORMATION FOR SEQ ID NO:114:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:114:

CGCGGGGAG TATTGCGGAG GGCG 24

( 2 ) INFORMATION FOR SEQ ID NO:115:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:115:

CCTGGGGGAG TATTGCGGAG GAAGG 25

( 2 ) INFORMATION FOR SEQ ID NO:116:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:116:

CGCGGGGGAG TATTGCGGAG GAGCG 25

( 2 ) INFORMATION FOR SEQ ID NO:117:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:117:

CCTGGGGGAG TATTGCGGAG GAAGG 25

( 2 ) INFORMATION FOR SEQ ID NO:118:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:118:

CGCGGGGGAG TATTGCGGAG GAGCG                                                                25

( 2 ) INFORMATION FOR SEQ ID NO:119:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:119:

CCTGGGGGGG AGTATTGCGG GAGGGAAGG                                                            29

( 2 ) INFORMATION FOR SEQ ID NO:120:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:120:

CCTGGGGGGG AGTATTGCGG GAGGGAAGG                                                            29

( 2 ) INFORMATION FOR SEQ ID NO:121:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:121:

CCTGGAGGAG TATAT                                                                           15

( 2 ) INFORMATION FOR SEQ ID NO:122:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:122:

ATAGCGGAGG AAGG                                                                            14

( 2 ) INFORMATION FOR SEQ ID NO:123:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:123:

ATTATAGCGG AGGAAGGTAT                                                                      20

( 2 ) INFORMATION FOR SEQ ID NO:124:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:124:

```
ATACCTGGGG GAGTATATAA T                                       21
```

( 2 ) INFORMATION FOR SEQ ID NO:125:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:125:

```
CCTGGGGAGG CGTTATGAGA AGG                                     23
```

( 2 ) INFORMATION FOR SEQ ID NO:126:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:126:

```
CCTGGGGAGG GCGTTATGGG GGGAAGG                                 27
```

( 2 ) INFORMATION FOR SEQ ID NO:127:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:127:

```
ATAGCGGAGG GGTCCATAGG AAGGTATAT                               29
```

( 2 ) INFORMATION FOR SEQ ID NO:128:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:128:

```
ATTATAGCGG AGGGGTCCAT ATATGGAAGG TATATAAT                     38
```

( 2 ) INFORMATION FOR SEQ ID NO:129:

( i ) SEQUENCE CHARACTERISTICS:
        ( A ) LENGTH: 24 base pairs
        ( B ) TYPE: nucleic acid -continued

```
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:129:
```

CCTGGTTGTG GCGTTATGGG AAGG                                                            24

( 2 ) INFORMATION FOR SEQ ID NO:130:

```
        ( i ) SEQUENCE CHARACTERISTICS:
            ( A ) LENGTH: 142 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:130:
```

ACAGGACTCA TCTACGCACC NNNNNNNNNN NNNNNNNNNN NNNNNNNNNN NNNNNNNNNN       60

NNNNNNNNNN NNNNNNNNNN AGTCGGGGGG AGTAGCANNN NNNNNNNNNN NNNNNNNNNN      120

NNGGCACCGG AACACTATCC GA                                              142

( 2 ) INFORMATION FOR SEQ ID NO:131:

```
        ( i ) SEQUENCE CHARACTERISTICS:
            ( A ) LENGTH: 141 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:131:
```

AACACTATCC GACTGGCACC NNNNNNNNNN NNNNNNNNNN NNNNNTGCAC GGAGGACGAC       60

TNNNNNNNNN NNNNNNNNNN NNNNNNNNNN NNNNNNNNNN NNNNNNNNNN NNNNNNNNNN      120

NAGTTTGGGT ATTAGCCGAA G                                               141

( 2 ) INFORMATION FOR SEQ ID NO:132:

```
        ( i ) SEQUENCE CHARACTERISTICS:
            ( A ) LENGTH: 208 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:132:
```

NNNNNNNNNN NNNNNNNNNN NNNNNNNNNN NNNNNNNNNN NNNNNNNNNN NNNNNNNNNN       60

AGTCGGGGGG AGTAGCANNN NNNNNNNNNN NNNNNNNNNN NNGGCACCNN NNNNNNNNNN      120

NNNNNNNNNN NNNTGCACGG AGGACGACTN NNNNNNNNNN NNNNNNNNNN NNNNNNNNNN      180

NNNNNNNNNN NNNNNNNNNN NNNNNNN                                         208

( 2 ) INFORMATION FOR SEQ ID NO:133:

```
        ( i ) SEQUENCE CHARACTERISTICS:
            ( A ) LENGTH: 42 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:133:
```

```
GTGCTTGGGG GAGTATTGCG GAGGAAAGCG GCCCTGCTGA AG                                    42
```

( 2 ) INFORMATION FOR SEQ ID NO:134:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:134:

```
GGAACACTAT CCGACTGGCA CC                                                         22
```

( 2 ) INFORMATION FOR SEQ ID NO:135:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:135:

```
CCTTGGTCAT TAGGATCC                                                              18
```

( 2 ) INFORMATION FOR SEQ ID NO:136:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:136:

```
GCGGAATTCG GAACACTATC CGACTGGCAC C                                               31
```